(12) United States Patent
Kodama et al.

(10) Patent No.: US 6,423,943 B1
(45) Date of Patent: Jul. 23, 2002

(54) CONNECTING CLAMP, CONNECTING APPARATUS AND CONNECTING METHOD

(75) Inventors: Masaru Kodama; Kiyotaka Iwatsubo; Nobuhiko Nishimura, all of Nagasaki; Toshihiko Imamoto; Masaaki Fujita, both of Tokyo, all of (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/933,664

(22) Filed: Aug. 22, 2001

Related U.S. Application Data

(62) Division of application No. 09/634,323, filed on Aug. 7, 2000.

(30) Foreign Application Priority Data

Aug. 11, 1999 (JP) ............................................. 11-228038
Nov. 2, 1999 (JP) ............................................. 11-313007

(51) Int. Cl.[7] ........................... B23K 3/08; B23K 20/14; G01N 29/10
(52) U.S. Cl. .......................... 219/243; 285/41; 285/420; 219/535; 219/611
(58) Field of Search ................................. 219/243, 535, 219/611; 285/41, 420; 228/212

(56) References Cited

U.S. PATENT DOCUMENTS

| | | | | |
|---|---|---|---|---|
| 1,894,835 A | * | 1/1933 | Smith et al. ................. | 219/611 |
| 2,678,370 A | * | 5/1954 | Denneen ...................... | 219/611 |
| 2,919,335 A | * | 12/1959 | Shaughnessy ................ | 219/611 |
| 3,031,554 A | * | 4/1962 | Jackson ....................... | 219/611 |
| 3,065,536 A | * | 11/1962 | Chapman ..................... | 228/212 |
| 3,644,695 A | * | 2/1972 | Shuey, Jr. et al. ........... | 219/611 |

FOREIGN PATENT DOCUMENTS

| | | | | |
|---|---|---|---|---|
| JP | 54-1651 | * | 1/1979 | .................. 219/611 |
| JP | 61-137679 | | 6/1986 | |
| JP | 62-097784 | | 5/1987 | |
| JP | 2-97991 | | 8/1990 | |
| JP | 3-071950 | | 11/1991 | |
| JP | 5-288722 | | 11/1993 | |
| JP | 6-063771 | | 3/1994 | |
| JP | 8-136512 | | 5/1996 | |
| JP | 9-318604 | | 12/1997 | |

* cited by examiner

*Primary Examiner*—John A. Jeffery
(74) *Attorney, Agent, or Firm*—Oblon, Spivak, McClelland, Maier & Neustadt, P.C.

(57) ABSTRACT

A connecting clamp includes a heating member which surrounds a portion to be connected of a steel pipe and heats the portion to be connected, and a first clamp section and second clamp section positioned on opposite sides of the portion to be connected and clamping the steel pipe, whereby the portion to be connected is connected by heating the portion to be connected by the heating member while applying pressure to the portion to be connected by the first and second clamp sections. The first and second clamp sections and the heating member are so arranged as to be slid around the outer surface of the steel pipe from one side of the steel pipe to the other side thereof.

5 Claims, 25 Drawing Sheets

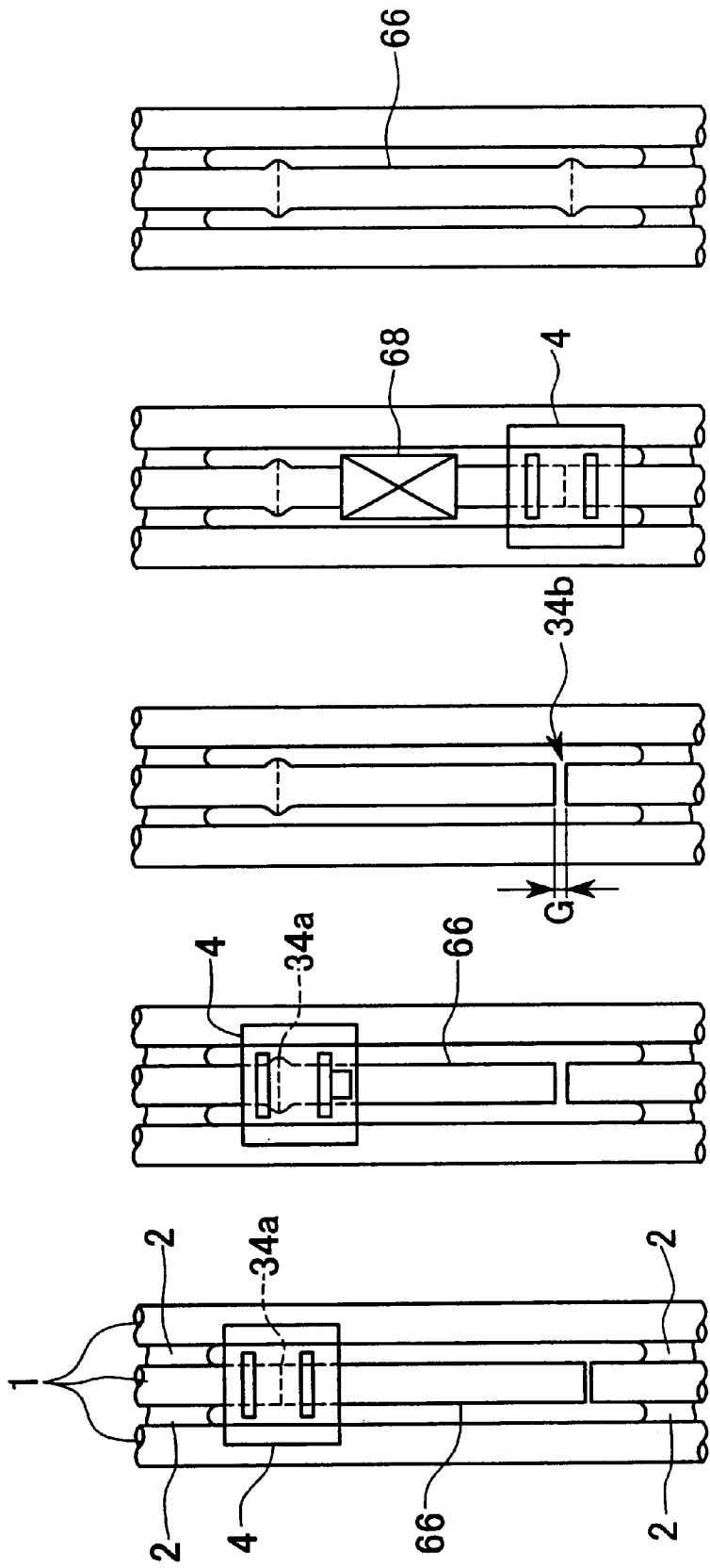

PRIOR ART

PRIOR ART

PRIOR ART

PRIOR ART

CONNECTING CLAMP, CONNECTING APPARATUS AND CONNECTING METHOD

This application is a Division of application Ser. No. 09/634,323 Filed on Aug. 7, 2000.

BACKGROUND OF THE INVENTION

1. Field of the Invention

The present invention relates to a connecting clamp, connecting apparatus and connecting method, which are suitable for use at the time of joining a portion to be connected of a rod-like member, such as a metal pipe, by using a diffusion bonding method. This invention also relates to an ultrasonic detecting method and ultrasonic detecting apparatus, which are effective in inspecting defects on a surface joined by diffusion bonding. This application is based on Japanese Patent Applications No. Hei 11-228038 and No. Hei 11-313007, the contents of which are incorporated herein by reference.

2. Description of the Related Art

FIG. 28 shows an example of the structure of a furnace wall which is used in a plant or the like. This wall portion is a combination of a plurality of steel pipes 1 provided upright in parallel to one another with small distances therebetween and fins 2 provided between the individual steel pipes 1.

When damage 3 occurs in one of the steel pipes 1 and mending, such as bonding is required, it is difficult for a worker to access that portion of the damage 3 which faces towards the inside of the furnace because of the small distances between the steel pipes 1. To permit access to the damage not only from outside the furnace but also from inside, conventionally, welding was carried out after a scaffold 101 was set up inside the furnace as shown in FIGS. 29 and 30. Because putting up the scaffold 101 is time consuming, the mending takes a considerable time.

Conventionally, fusion welding in which a base metal 250 is cut into a V shape and padding is applied between the cut surfaces by welding has been common in bonding metal materials including iron and steel. A typical means for detecting a welding defect F at the padding is a P/S (Pulse Signal) probe type ultrasonic detecting apparatus which combines an ultrasonic transmitting element and an ultrasonic receiving element. As shown in FIG. 32, this ultrasonic detecting apparatus irradiates an ultrasonic wave perpendicular to the welded surface and receives the ultrasonic wave that returns through the same path, in order to detect a welding defect. The above fusion welding method requires several cutting processes and deforms the welded portion or thermally changes the composition. Securing a reliable welded portion with this method therefore requires highly skilled work and is costly.

Recently, there has been interest in the diffusion bonding method as one solution to the above problem. In this diffusion bonding method, an easily-diffusible thin metal sheet is positioned between the surfaces to be connected, and high temperature and pressure are applied to the portion near the surfaces to be connected in such a way that there is little plastic deformation, thereby diffusing atoms between the surfaces to be connected to accomplish bonding. Diffusion bonding has the advantages that it does not require any special skill and shows excellent performance, does not deform the outline of the connected surface and provides a connected surface with a uniform composition (see Japanese Unexamined Patent Application, First Publication No. 62-97784).

One metal-liquid phase diffusion bonding method which has been proposed is an amorphous bonding method which uses an amorphous sheet. This amorphous bonding method will now be discussed briefly with reference to the case where a steel pipe is bonded using an amorphous sheet containing boron which reduces the melting point. The amorphous sheet is a thin sheet made by rapid solidification and has a thickness of about 25 $\mu$m.

First, an amorphous sheet whose composition is similar to that of a steel pipe (base metal) and which contains boron is inserted between the surfaces to be connected. Then, the amorphous sheet is heated to a temperature equal to or lower than the melting point of the base metal and equal to or higher than the melting point of the amorphous sheet. Consequently, boron in the amorphous sheet is diffused in the parent phase, lowering the melting point of the parent phase and melting the parent phase. When heating is maintained in that condition, further diffusion of boron lowers the concentration of boron. This raises the melting point of the parent phase, so that the parent phase is gradually solidified, thus achieving bonding.

This bonding method has several advantages, such as a shorter bonding time, a simpler connecting apparatus structure and a lower heating temperature as compared with the conventional welding.

An apparatus which implements this amorphous bonding method will be described briefly with reference to FIG. 31.

First, an amorphous sheet 72 is inserted between ends to be joined at the portion to be connected 34 of a steel pipe 1. Next, the upper and lower steel pipes 1 are held by a clamp (not shown) and are urged in the directions of the arrows so as to push together the portion to be connected 34. A high-frequency heating coil 104 heats the portion to be connected 34 which is under pressure from the clamp. The high-frequency heating coil 104 heats the portion to be connected 34 at a temperature equal to or higher than the melting point of the amorphous sheet 72 and equal to or lower than the melting point of the steel pipe 1. The aforementioned amorphous bonding is carried out in this way.

However, the conventional apparatus does not operate on the premise of bonding of one of a plurality of steel pipes 1 that are arranged with the small distances therebetween, as mentioned previously. That is, steel pipes can be bonded by this apparatus when sufficient working space can be provided around the steel pipes 1, whereas if a plurality of steel pipes 1 are arranged with small distances therebetween, sufficient working space cannot be secured around each steel pipe 1, and as a result, a high-frequency heating coil or the like cannot be set around the steel pipe 1.

As the joined or connected surface is formed perpendicular to the material surface according to the diffusion bonding method, an ultrasonic wave cannot be irradiated perpendicular to the connected surface for detecting a welding defect F in the connected surface formed by the diffusion bonding method. This disables the use of a P/S probe type ultrasonic detecting apparatus which combines an ultrasonic transmitting element and ultrasonic receiving element. One method which uses the conventional P/S probe type ultrasonic detecting apparatus has been proposed in, for example, Japanese Unexamined Patent Application, First Publication No. 6-63771. According to this method, as shown in FIG. 33, surfaces to be connected are so cut as to have certain angles and are butted so that an ultrasonic wave can be irradiated perpendicular to the connected surface. However, this method is not practical because it is difficult to cut the base metal.

Ultrasonic inspection of a connected surface formed perpendicular to the surface of the base metal can be carried out by a double-probe method which has an ultrasonic transmitting element and ultrasonic receiving element separately installed in two probes as shown in FIG. 34.

This double-probe method uses an ultrasonic transmitting element and an ultrasonic receiving element separate from each other, reflects an ultrasonic wave inside the base metal to irradiate the ultrasonic wave on the connected surface at a predetermined angle, reflects the ultrasonic wave, reflected at the connected surface, in the base metal again and receives it at the receiving element.

However, the conventional double-probe method has a long propagation path for the ultrasonic wave in the base metal and uses multiple reflections which significantly attenuates the ultrasonic wave. What is more, because noise is occurs at every reflection, the sensitivity to detect minute defects is diminished. Those disadvantages make the conventional double-probe method impractical.

Accordingly, it is an object of the present invention to provide a connecting clamp, a connecting apparatus and a connecting method, which can allow a clamp section and heating member to be positioned around a rod member, such as a steel pipe, even if ample working space cannot be secured around the rod member. It is another object of this invention to provide an ultrasonic detecting method for inspecting a diffusion-bonded surface which has undergone simple material processing and which has a significantly improved defect detecting performance, and an apparatus which implements this method. It is a further object of this invention to provide an ultrasonic detector which is effective in inspecting a bonding defect at a diffusion-bonded portion of, particularly, a steel pipe.

SUMMARY OF THE INVENTION

A connecting clamp according to one aspect of this invention comprises a heating member which surrounds a portion to be connected of a rod member and heats the portion to be connected; and a first clamp section and a second clamp section positioned on opposite sides of the portion to be connected and clamping the rod member, whereby the portion to be connected is connected by heating the portion to be connected by the heating member while applying pressure to the portion to be connected by the first and second clamp sections, and is characterized in that the first and second clamp sections and the heating member are so arranged as to be slid around an outer surface of the rod member from one side of the rod member to the other side thereof. Note that the "rod member" includes a solid rod as well as a tubular member such as a steel pipe.

A connecting clamp according to another aspect of this invention, which connects a portion to be connected by heating it by means of a heating member, is characterized in that first and second clamp sections are so arranged as to be slid around an outer surface of the rod member from one side of the rod member to the other side thereof, the heating member has a heating coil so provided as to surround the rod member, the heating coil having a curved portion curved in one plane in such a way as to have an inside diameter slightly greater than an outside diameter of the rod member and an opening larger than the outside diameter.

In this case, it is desirable that each of the first and second clamp sections and the heating member should have a tubular shape and should comprise a plurality of components which are separable along the radial direction of the tubular shape. The number of separable components has only to be equal to or greater than two, and the separable components can have any size. The tubular shape may take any shape, such as a cylinder or a shape has a rectangular cross section, as long as it can surround a rod member.

It is further desirable that the first and second clamp sections and the heating member should have holding levers for respectively holding the first and second clamp sections and the heating member at the time of sliding the first and second clamp sections and the heating member around the outer surface of the rod member.

Further, it is desirable that the heating member should be further provided with a cooling pipe and a shield-gas feeding pipe, and each of the cooling pipe and the shield-gas feeding pipe should have a curved portion curved in one plane in such a way as to have an inside diameter slightly greater than the outside diameter of the rod member and an opening larger than the outside diameter.

The heating member may be constituted by stacking a plurality of shield-gas feeding pipes, a plurality of cooling pipes and a plurality of heating coils. In this case, as a plurality of shield-gas feeding pipes, a plurality of cooling pipes and a plurality of heating coils are stacked one on another, and they can be combined adequately in accordance with the condition of the portion to be connected of the rod member.

A connecting apparatus according to a further aspect of this invention comprises the above-described connecting clamp; a pressure applying means for applying pressure to the first and second clamp sections so as to urge them towards each other; and a power source for supplying power to the heating member.

A connecting method according to a still further aspect of this invention comprises a wax-material positioning stage of positioning a wax material between connecting ends at a portion to be connected of a rod member; a clamp-section attaching stage of positioning a first clamp section and a second clamp section on opposite sides of the portion to be connected and attaching the first and second clamp sections to the rod member; and a heating-member attaching stage of attaching a heating member in such a way as to surround the portion to be connected; and a connecting stage of connecting the portion to be connected by heating the portion to be connected by the heating member while applying pressure to the portion to be connected by the first and second clamp sections, the clamp-section attaching stage including a step of arranging the first and second clamp sections so as to be slid around an outer surface of the rod member from one side of the rod member to the other side thereof, the heating-member attaching stage including a step of arranging the heating member so as to be slid around the outer surface of the rod member from the one side of the rod member to the other side thereof.

The above-described connecting method of this invention is characterized in that the heating member is provided with a heating coil, a cooling pipe and a shield-gas feeding pipe, and each of the heating coil, the cooling pipe and the shield-gas feeding pipe having a curved portion curved in one plane in such a way as to have an inside diameter slightly greater than the outside diameter of the rod member and an opening larger than the outside diameter, and the heating-member attaching stage includes a stage of moving the heating coil, the cooling pipe and the shield-gas feeding pipe forward in such a way that said plane is approximately parallel to the upright-standing direction of the rod member to thereby guide the curved portions from a front side of the rod member toward a rear side thereof, and a stage of rotating said plane in such a way as to become perpendicular the upright-standing direction, so that the curved portions surround the portion to be connected.

It is desirable that the connecting stage should include a step of heating the rod member so that a distance between the connecting ends of the portion to be connected is decreased by thermal expansion of the rod member. Further, the wax-material positioning stage may include a step of positioning an insert member between the connecting ends and positioning the wax material between the insert member and each of the connecting ends.

According to a still further aspect of this invention, an ultrasonic detecting method using a double-probe method in which a transmitting element and a receiving element are separated from each other, directly irradiates an ultrasonic wave onto a surface to be probed inside a material at a predetermined angle, receives a reflected ultrasonic wave after being reflected inside the material once and performs probing while adequately changing the distance between the transmitting element and the surface to be probed and the distance between the transmitting element and the receiving element, whereby an internal defect present along the inspected surface perpendicular to the surface of the material can be detached.

As an apparatus which is used in this method, according to this invention, an ultrasonic detecting apparatus has been developed which comprises a transmitting element for emitting an ultrasonic wave towards a surface to be probed inside a sample from a surface of the sample at a predetermined angle; and a receiving element for receiving the ultrasonic wave reflected from the surface of the sample, the transmitting element and the receiving element being separated from each other on a single pedestal, wherein the transmitting element and the receiving element are movable on the surface of the sample in a direction perpendicular to the surface to be proved, and the distance between the transmitting element and the receiving element is arbitrarily changeable.

This ultrasonic detecting apparatus can be provided with a supplemental unit for ensuring efficient ultrasonic detection of a pipe member, such as a roller which is attached to the pedestal of the ultrasonic detecting apparatus so that the apparatus is movable around the pipe member, or a magnet which causes the ultrasonic detecting apparatus to be always attracted to a steel pipe and prevents the apparatus from coming off the steel pipe, at the time of inspecting the steel pipe, or an encoder attached to the pedestal so that the moving distance around the pipe member can be determined. To facilitate inspection of the outer surface of a pipe, the signal line of the probe and the signal line of the encoder may be made of a shape memory alloy which memorizes the same curvature as the pipe's diameter.

BRIEF DESCRIPTION OF THE DRAWINGS

FIG. 16A is a front view illustrating a connecting method according to this invention and showing a connecting clamp positioned at an upper portion to be connected;

FIG. 16B is a front view illustrating the connecting method according to this invention and showing the upper portion to be connected in the connected state;

FIG. 16C is a front view illustrating the connecting method according to this invention and showing a gap produced in a lower portion to be connected;

FIG. 16D is a front view illustrating the connecting method according to this invention and showing the connecting clamp positioned at the lower portion to be connected;

FIG. 16E is a front view illustrating the connecting method according to this invention and showing that the connecting work has been completed;

DETAILED DESCRIPTION OF THE PREFERRED EMBODIMENTS

First Embodiment

Figure 1:
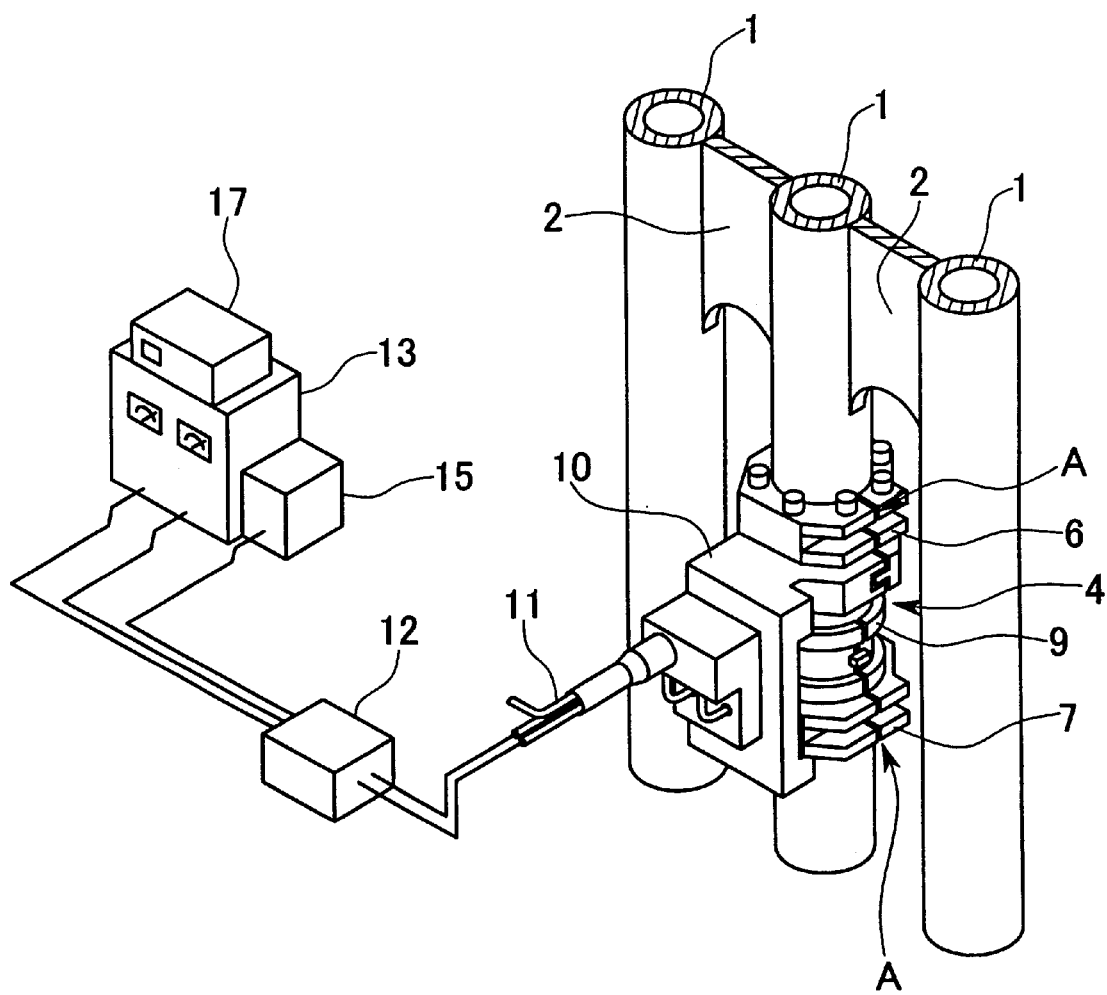
FIG. 1 is a perspective view of a first embodiment of this invention, illustrating a connecting apparatus attached to a steel pipe.

FIG. 1 is a perspective view illustrating a connecting apparatus according to the first embodiment of this invention.

Reference numeral "1" denotes a steel pipe (rod member) and reference numeral "2" denotes a fin which connects the individual steel pipes 1. Referring to the diagram, a part of the fin 2 on either side of the center steel pipe 1 is removed by a predetermined method so that a heating member to be discussed later or the like can be attached to a portion to be connected which requires mending. A connecting clamp 4 is attached to the steel pipe 1 at the portion where the fins 2 have been removed. The connecting clamp 4 has an upper clamp section (first clamp section) 6, a lower clamp section (second clamp section) 7 and a heating member 9 provided between the upper and lower clamp sections 6 and 7 and is formed as an integral, movable unit. Attached to the heating member 9 is a connecting head portion 10 which is provided with a thermometer 11 for measuring the temperature near the portion to be connected.

The upper clamp section 6 and the lower clamp section 7 are pressed towards each other by a hydraulic system (pressure applying unit), not shown.

Though not shown, the heating member 9 accommodates a high-frequency heating coil for heating the portion to be connected with frequency, a cooling pipe for cooling this heating coil and a shield-gas feeding pipe for feeding a shield gas, such as argon gas, to prevent oxidation of the portion to be connected. The heating coil is supplied with power from a high-frequency power source 13 via a matching transformer 12 for impedance matching.

A water cooling unit 15 which cools the matching transformer 12 is provided on one side of the high-frequency power source 13. Placed on the top of the high-frequency power source 13 is a controller 17 which controls the supply power or the like based on the output value of the thermometer 11.

As apparent from FIG. 1, the upper clamp section 6, the lower clamp section 7 and the heating member 9 in the above-described structure are separable along the radial direction at a position indicated by a reference symbol "A"; they are separated into two components in this embodiment.

The following will discuss how to connect the steel pipe 1 using the above-described apparatus.

First, the upper clamp section 6 and the lower clamp section 7 are positioned on the opposite sides of a portion to be connected (not shown) of the steel pipe 1 and are secured to the steel pipe 1. In this case, as the upper and lower clamp sections 6 and 7 are separated into components, the components are slid around the target steel pipe 1 from the front side (one side) of the steel pipe 1 to the rear side (the other side) through a small distance between the steel pipe 1 and an adjoining steel pipe 1. Though not shown, a boron-containing amorphous sheet (wax material) having a thickness of about 25 μm is inserted between the ends to be joined of the portion to be connected of the steel pipe 1.

Next, the heating member 9 is attached between the upper clamp section 6 and the lower clamp section 7 in such a way as to surround the portion to be connected. As the heating member 9 is also separated into components, the components are slid around the target steel pipe 1 from the front side of the steel pipe 1 to the rear side through the small distance between the steel pipe 1 and the adjoining steel pipe 1. The structures of the separated components and method of attaching the components will be described in more detail later under the second embodiment. Then, the connecting head portion 10 is attached to the heating member 9 so that power can be supplied to the heating member 9 from the high-frequency power source 13.

Thereafter, the upper and lower clamp sections 6 and 7 are displaced in the direction so as to narrow the gap between the clamp sections 6 and 7 by the hydraulic system, thus pushing together the portion to be connected of the steel pipe 1. When power is supplied to the high-frequency heating coil of the heating member 9 from the high-frequency power source 13 under this situation, the portion to be connected is heated with the high-frequency. At this time, the supply power is adjusted by the controller 17 while monitoring the temperature near the portion to be connected by means of the thermometer 11.

As a result, the amorphous sheet is heated to or above the melting point and melted, thereby accomplishing amorphous bonding.

Second Embodiment

The second embodiment of this invention will now be explained with reference to FIGS. 2 to 6.

Figure 2:
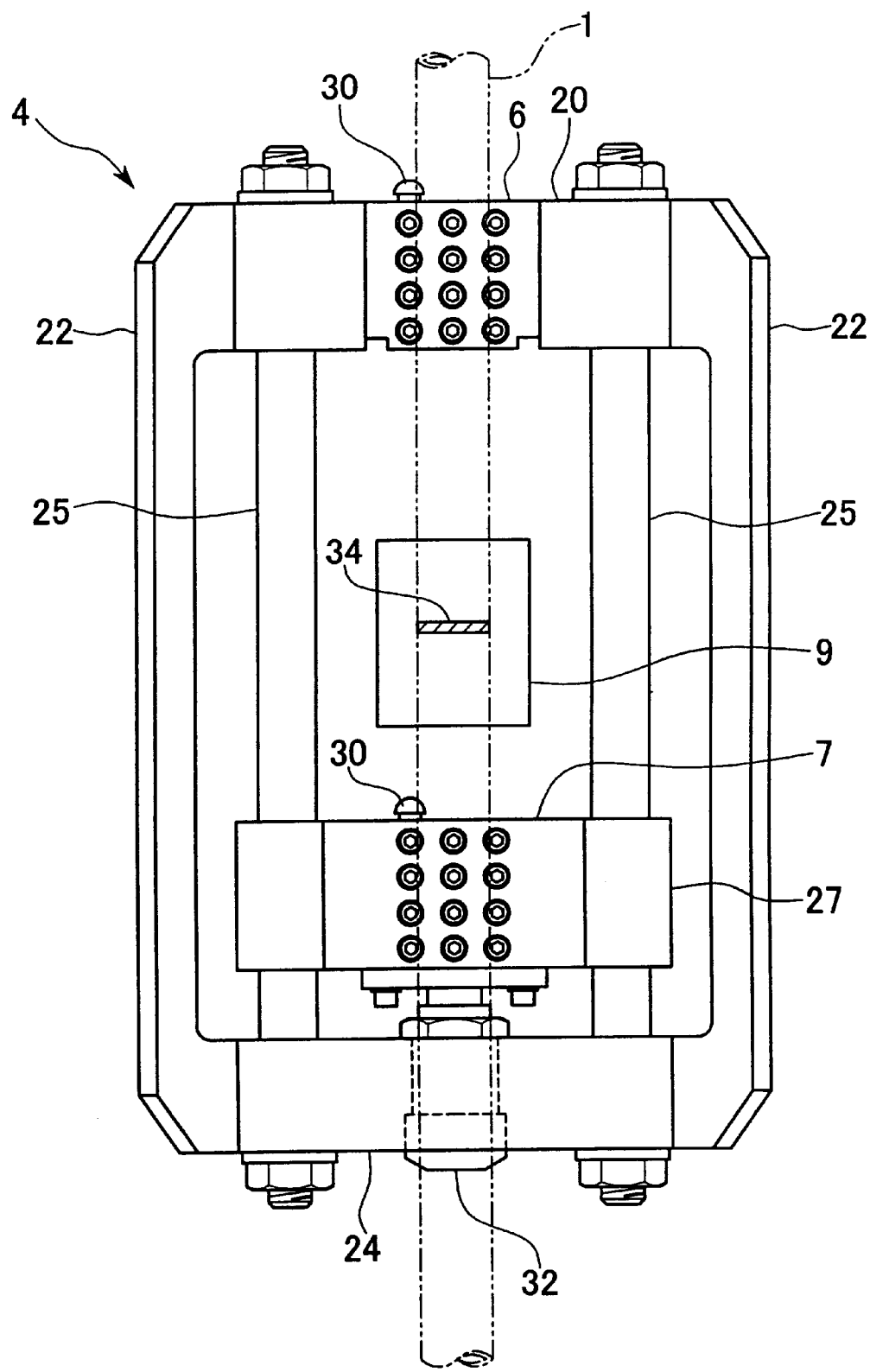
FIG. 2 is a front view of a connecting clamp according to a second embodiment of this invention.

FIG. 2 is a front view of the connecting clamp 4 according to the second embodiment. It is to be noted that like or the same reference numerals are given to those components which are common to the individual embodiments throughout the following description.

FIG. 2 shows the upper clamp section 6, the lower clamp section 7 and the heating member 9 attached to the steel pipe 1. The upper clamp section 6 is secured to an upper-clamp block 20 (see FIG. 3), which is coupled to a lower block 24 by means of arm portions 22 and 22 respectively provided on the right and left sides of the block 20. Two shaft members 25 and 25 are provided between the upper-clamp block 20 and the lower block 24 on the right and left sides to the steel pipe 1. Those shaft members 25 and 25 are movably inserted in a lower-clamp block 27 which is fixed to the lower clamp section 7 (see FIG. 2). That is, the lower-clamp block 27 and the lower clamp section 7 are movable relative to the shaft members 25 and 25.

Figure 3:
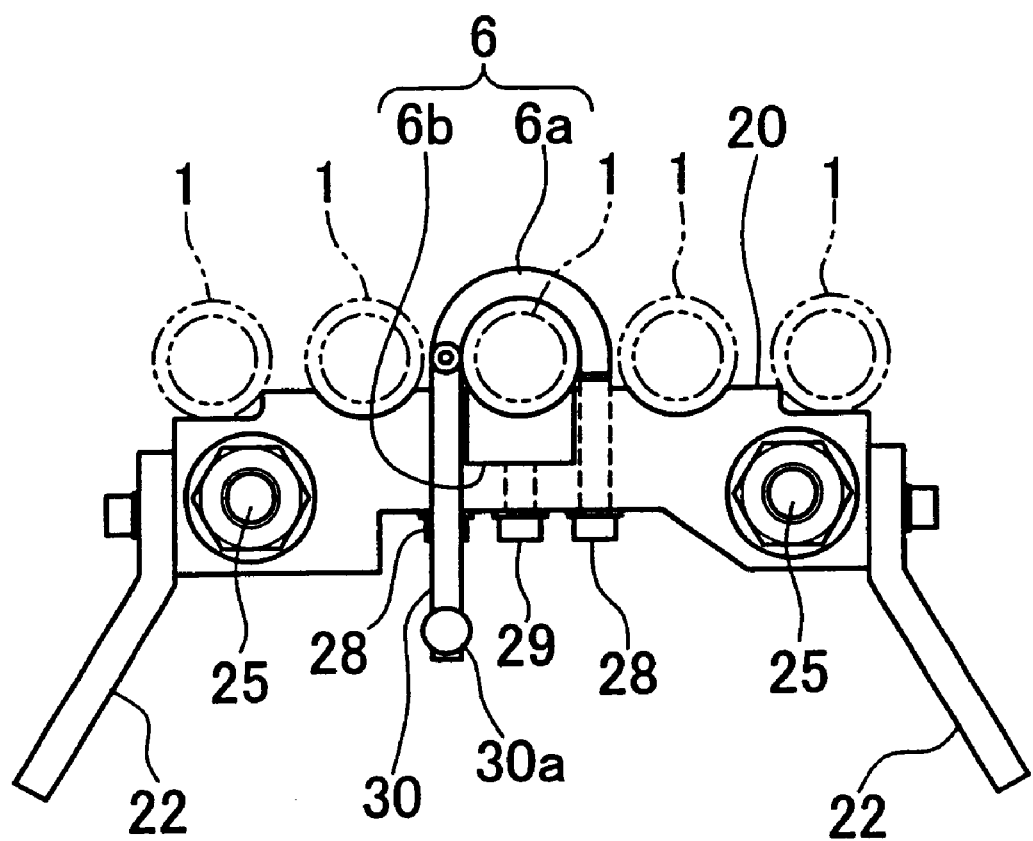
FIG. 3 is a plan view showing the details of a peripheral portion of an upper clamp section shown in FIG. 2.

As shown in FIG. 3, the upper clamp section 6 comprises a back component 6a and a front component 6b. The back component 6a has an approximately half-cylindrical shape. The back component 6a is secured to the upper-clamp block 20 by bolts 28. That is, fastening the bolts 28 causes the back component 6a and the upper-clamp block 20 to sandwich the steel pipe 1.

The front component 6b is fixed to the upper-clamp block 20 and pressed against the steel pipe 1 by bolts 29. The inner surface of the front component 6b has a shape which matches the outer surface of the steel pipe 1. The back component 6a and front component 6b hold the steel pipe 1.

A holding lever 30 is rotatably attached to the upper end portion of the back component 6a, so that a worker can hold the back component 6a by holding the grip 30a of this holding lever 30.

The structures of the lower clamp section 7 and the lower-clamp block 27 are basically the sane as those of the upper clamp section 6 and the upper-clamp block 20, except in that a hydraulic screw cylinder 32 is fixed to the lower-clamp block 27. This hydraulic screw cylinder 32 is also fixed to the lower block 24. The hydraulic screw cylinder 32 pushes the lower-clamp block 27 and the lower clamp section 7 in the direction away from the lower block 24 (upwards in the diagram). When the lower-clamp block 27 and the lower clamp section 7 are pushed in this way, the lower block 24 is coupled to the upper clamp section 6 via the arm portions 22 and the upper-clamp block 20, so that the upper clamp section 6 and the lower clamp section 7 are urged towards each other. That is, pressure is applied to the portion to be connected 34, of the steel pipe 1 held between the upper and lower clamp sections 6 and 7.

Figure 4:
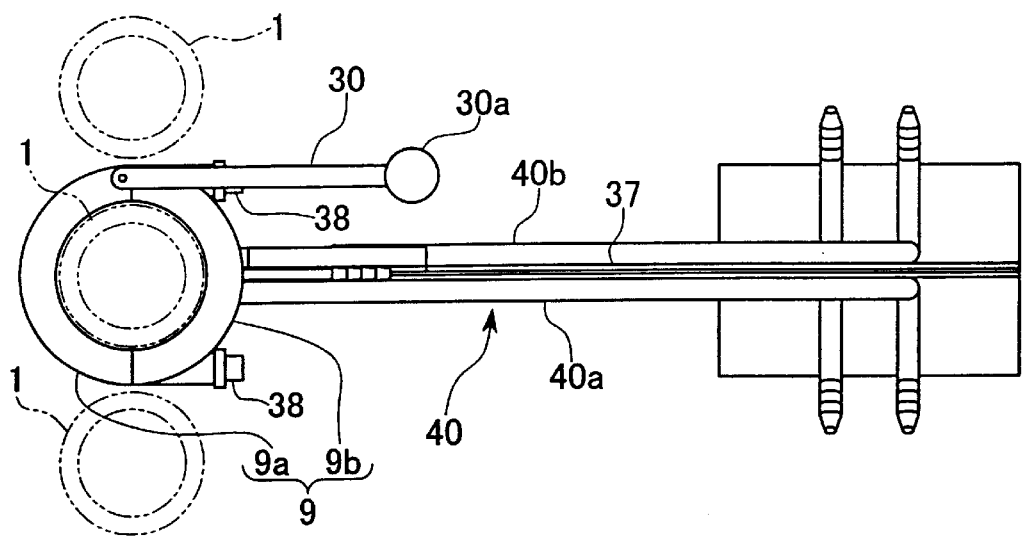
FIG. 4 is a plan view showing a heating coil in FIG. 2.
Figure 5:
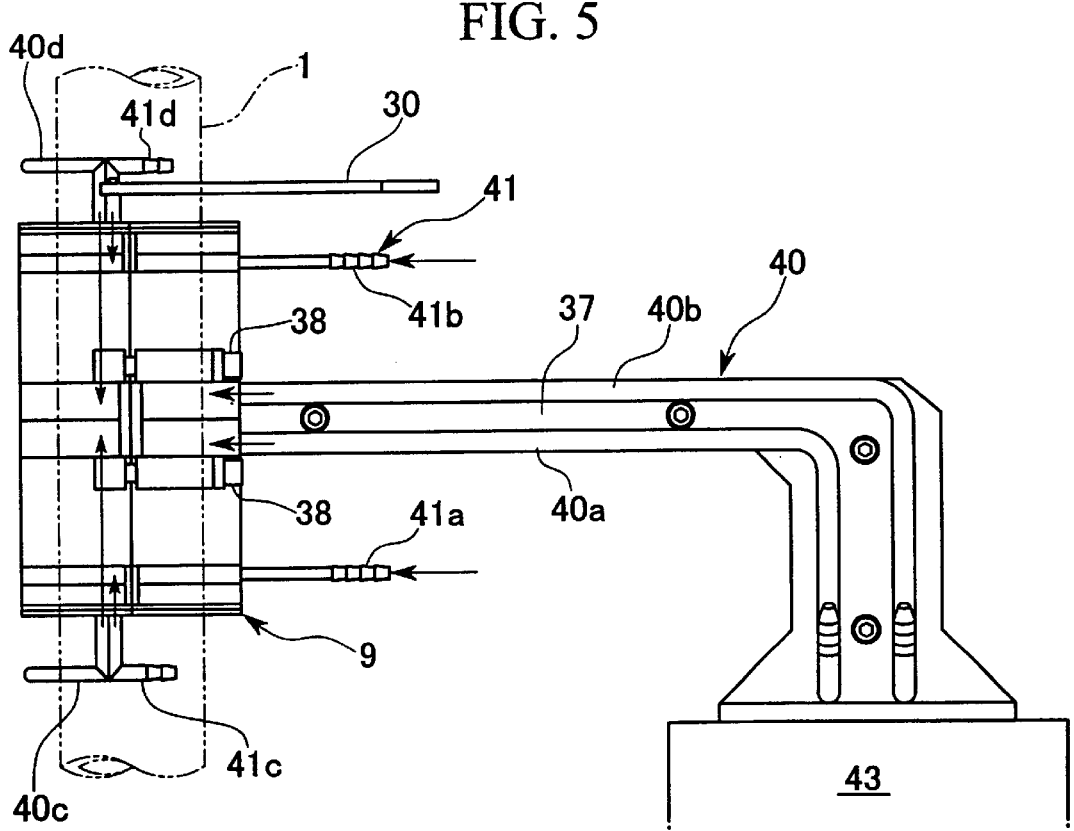
FIG. 5 is a side view showing the heating coil in FIG. 4.

With reference to FIGS. 4 and 5, a description will now be given of the heating member 9 which is so arranged as to surround the portion to be connected 34.

FIG. 4 is a plan view showing the heating member 9 and an L-shaped arm 37 coupled to this heating member 9. In this diagram, the heating member 9 is so arranged as to surround the steel pipe 1. The heating member 9 comprises a back component 9a and a front component 9b. The back component 9a and the front component 9b are secured to each other by bolts 38 as shown in FIG. 5. A holding lever 30 is rotatably attached to the upper end portion of the back component 9a, so that a worker can hold the back component 9a by holding a grip 30a of this holding lever 30.

Provided inside the heating member 9 are a cooling pipe 41 for feeding a coolant, a shield-gas feeding pipe 41 for feeding a shield gas, such as argon gas, to prevent oxidation of the portion to be connected, and a high-frequency heating coil (not shown).

FIGS. 4 and 5 show exposed portions of the cooling pipe 40 and the shield-gas feeding pipe 41. More specifically, as shown in FIG. 5, the cooling pipe 40 comprises a lower-right cooling pipe 40a for cooling the lower right portion of the heating member 9 in the diagram, an upper-right cooling pipe 40b for cooling the upper right portion of the heating member 9, a lower-left cooling pipe 40c for cooling the lower left portion of the heating member 9 and an upper-left cooling pipe 40d for cooling the upper left portion of the heating member 9. The shield-gas feeding pipe 41 likewise comprises a lower-right shield-gas feeding pipe 41a for blowing the shield gas to the lower right portion of the heating member 9, an upper-right shield-gas feeding pipe 41b for blowing the shield gas to the upper right portion of the heating member 9, a lower-left shield-gas feeding pipe 41c for blowing the shield gas to the lower left portion of the heating member 9, and an upper-left shield-gas feeding pipe 41d for blowing the shield gas to the upper left portion of the heating member 9. The arrows in FIG. 5 indicate the flow directions of the coolant and the shield gas.

The L-shaped arm 37 is made of a conductor and is electrically connected to a high-frequency power source 43 at the end opposite to the heating member 9 Therefore, power is supplied to the high-frequency heating coil via this L-shaped arm 37. As the L-shaped arm 37 is fixed to the high-frequency power source 43, it cantilevers the heating member 9.

Figure 6A:
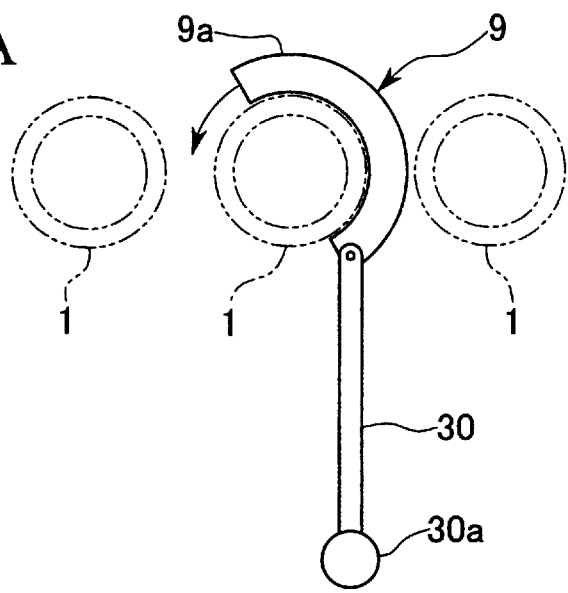
FIG. 6A is a plan view illustrating how to attach the heating coil which can slide.
Figure 6B:
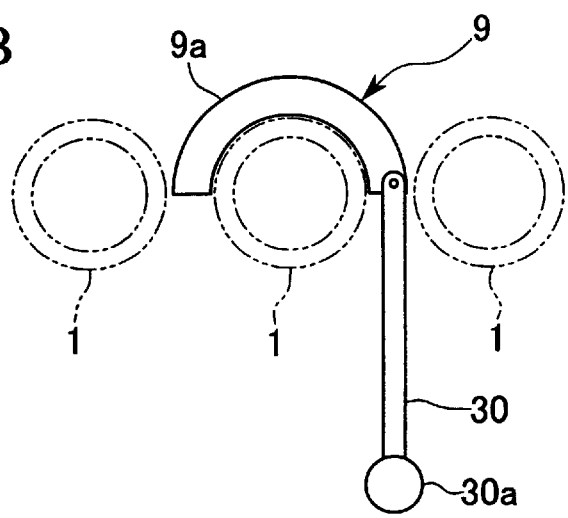
FIG. 6B is a plan view illustrating how to attach the heating coil which is set at a specific position.
Figure 6C:
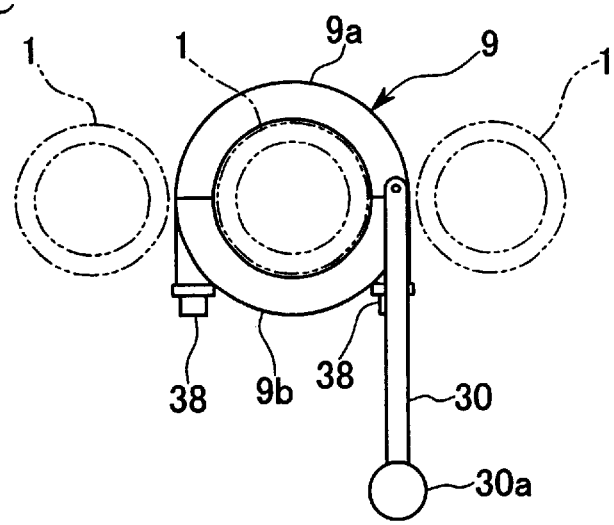
FIG. 6C is a plan view illustrating how to attach the heating coil which is secured at a specific position.

Referring now to FIGS. 6A to 6C, a description will be given of how to attach the heating member 9 to the steel pipe 1.

First, a worker holds the heating member 9 by holding the grip 30a of the holding lever 30 attached to the back component 9a. Then, the worker slides the back component 9a around the steel pipe 1 from the front side of the steel pipe to the rear side in such a way that the back component 9a passes between the steel pipe 1 and the adjoining steel pipe 1 (FIG. 6A).

The worker further slides the back component 9a to the position where the back component 9a is to be secured (FIG. 6B).

Then, the worker sets the front component 9b from the front side of the steel pipe 1 to mate with the back component 9a and secures the two together by the bolts 38 (FIG. 6C).

Designing the heating member 9 to be separate components 9a and 9b can allow the heating member 9 to pass between the steel pipes 1. In other words, even if the space between the target steel pipe 1 and the adjoining steel pipe 1 is limited, the components of the heating member 9 can be slid through the space if the radial thicknesses of the components are smaller than the space.

As the holding lever 30 is rotatably attached to the back component 9a, a worker remaining in front of the steel pipe 1 can set the back component 9a at the rear side of the steel pipe 1 from the front side. That is, the worker does not need to go around to the rear side of the steel pipe 1. Needless to say, the above-described attaching scheme is likewise applied to the upper and lower clamp sections 6 and 7.

Third Embodiment

The third embodiment of this invention will now be discussed with reference to FIGS. 7 to 14.

Figure 7:
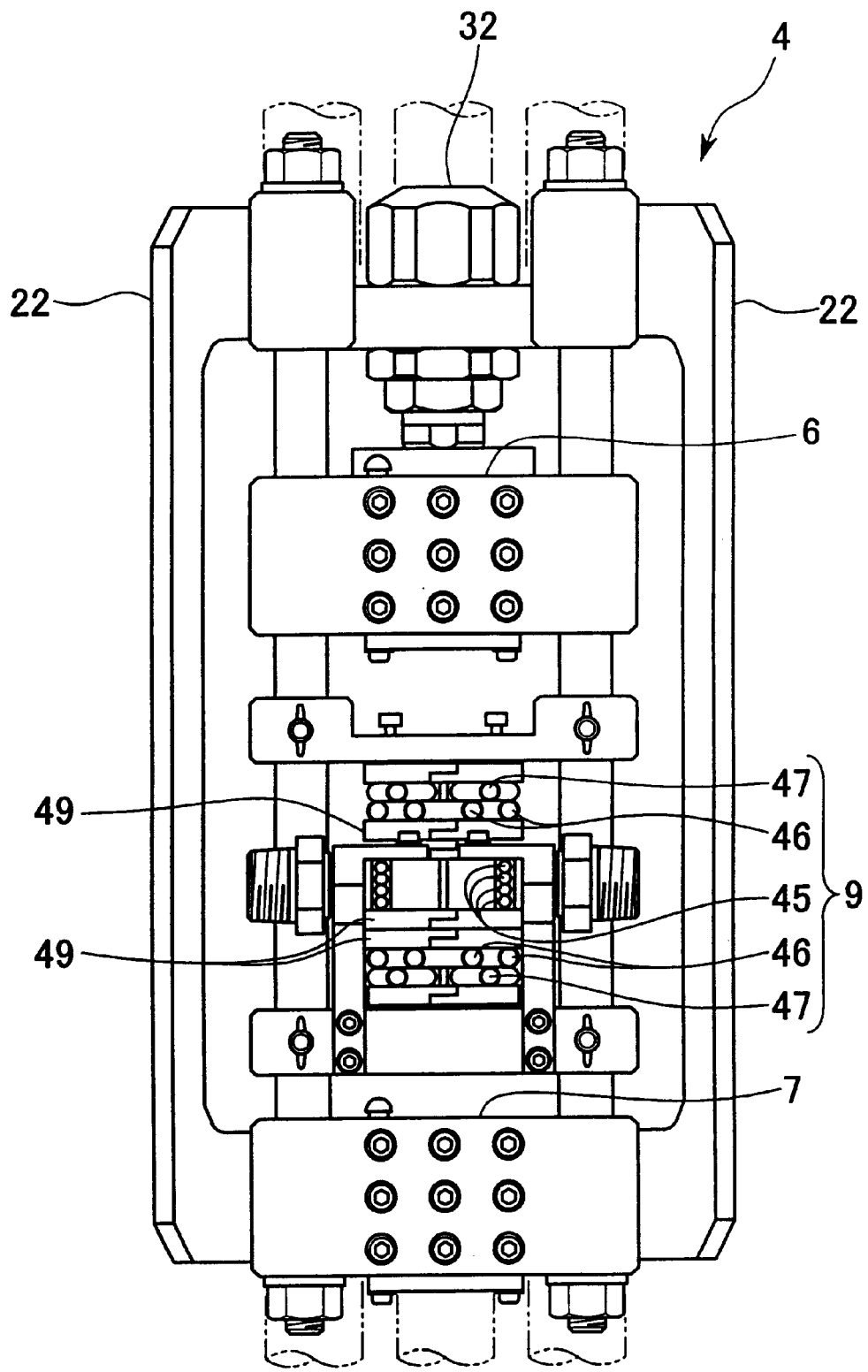
FIG. 7 is a front view depicting a connecting clamp according to a third embodiment of this invention.

FIG. 7 is a front view depicting the connecting clamp 4 according to the third embodiment. As the structures of the upper clamp section 6, the lower clamp section 7, the arm portions 22 and the hydraulic screw cylinder 32 of this connecting clamp 4 differ from those of the connecting clamp 4 that has been explained with reference to FIG. 2 only in that the connecting clamp 4 of the third embodiment is upside side down with respect to the connecting clamp 4 of the second embodiment, their descriptions will not be repeated. That is, the scheme of attaching the upper and lower clamp sections 6 and 7 in the third embodiment is the same as that in the second embodiment.

Figure 8:
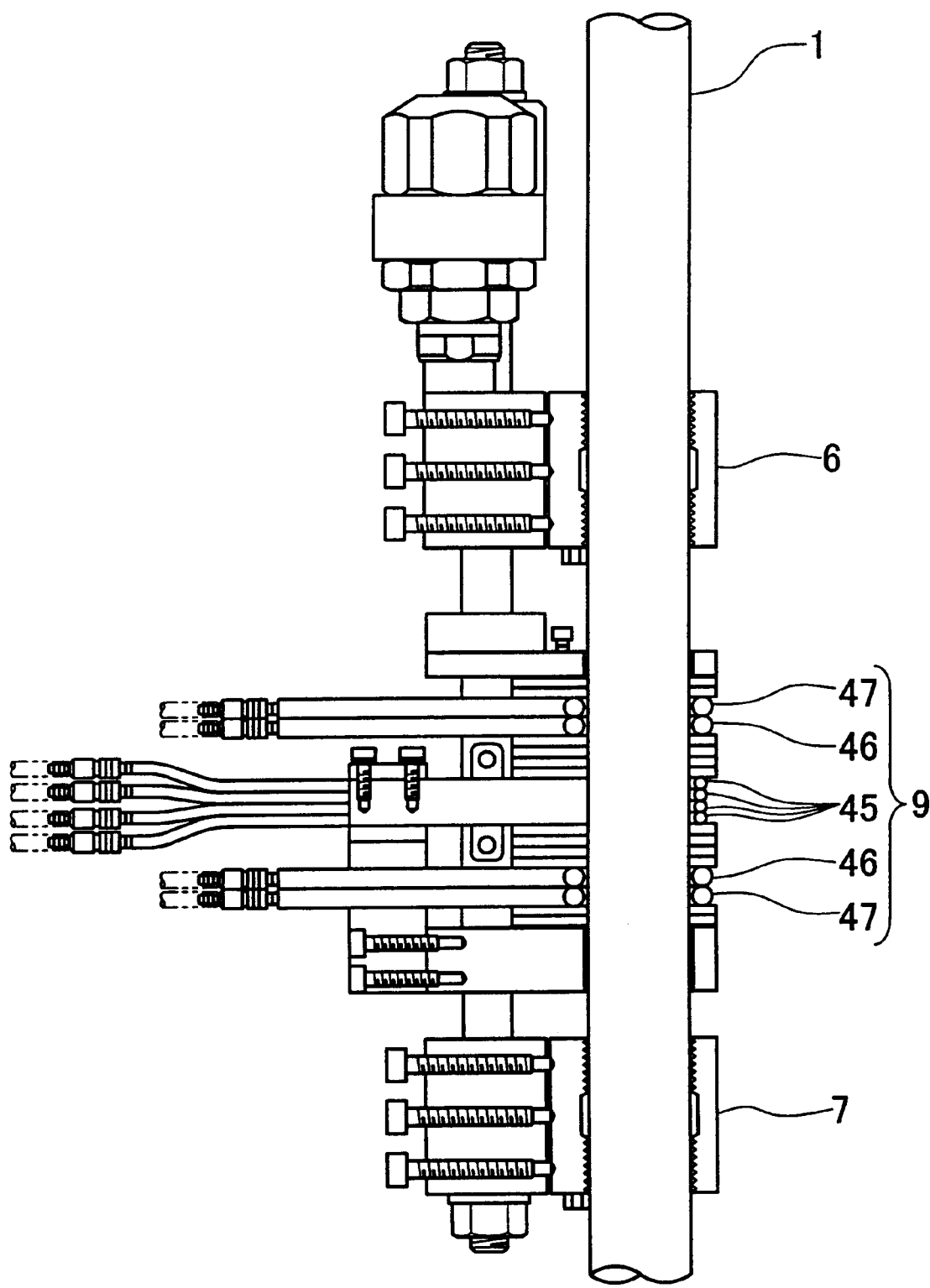
FIG. 8 is a cross-sectional view showing the connecting clamp in FIG. 7 cut in the axial direction.

As apparent from FIGS. 7 and 8, the heating member 9 of this embodiment comprises a lamination of a plurality of high-frequency heating coils 45, a plurality of cooling pipes 46 and a plurality of shield-gas feeding pipes 47. The cooling pipes 46 are positioned on and below the stack of the heating coils 45, and the shield-gas feeding pipes 47 are positioned on and the below the cooling pipes 46. A plurality of spacers 49 for electric insulation are positioned between the heating coils 45 and the cooling pipes 46.

Figure 9:
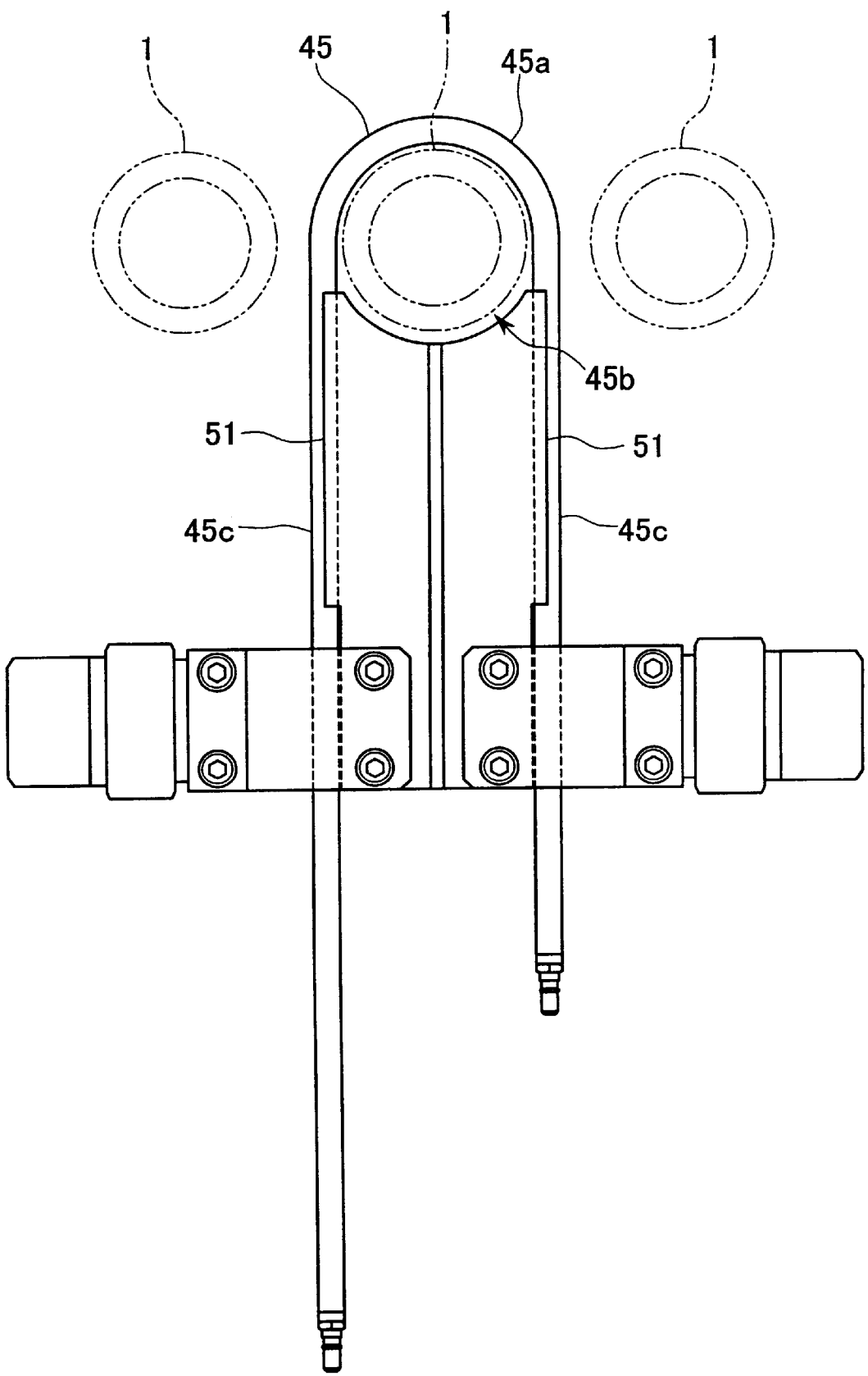
FIG. 9 is a plan view showing a heating coil in FIG. 7.

As shown in FIG. 9, each heating coil 45 comprises a U-shaped pipe of copper which has a curved portion 45a and in which cooling water can flow. The curved portion 45a is curved within one plane in such a way as to have an inside diameter slightly larger than the outside diameter of the steel pipe 1 and have an opening 45b larger than that outside diameter. The curved portion 45a is arranged at the back of the steel pipe 1 and a copper plate 51 is positioned in front of the steel pipe 1. As apparent from FIG. 9, this copper plate 51 is separated into right and left portions, which are electrically connected to respective right and left linear portions 45c of the heating coil 45. The curved portion 45a and copper plate 51 completely surround the steel pipe 1.

Figure 10:
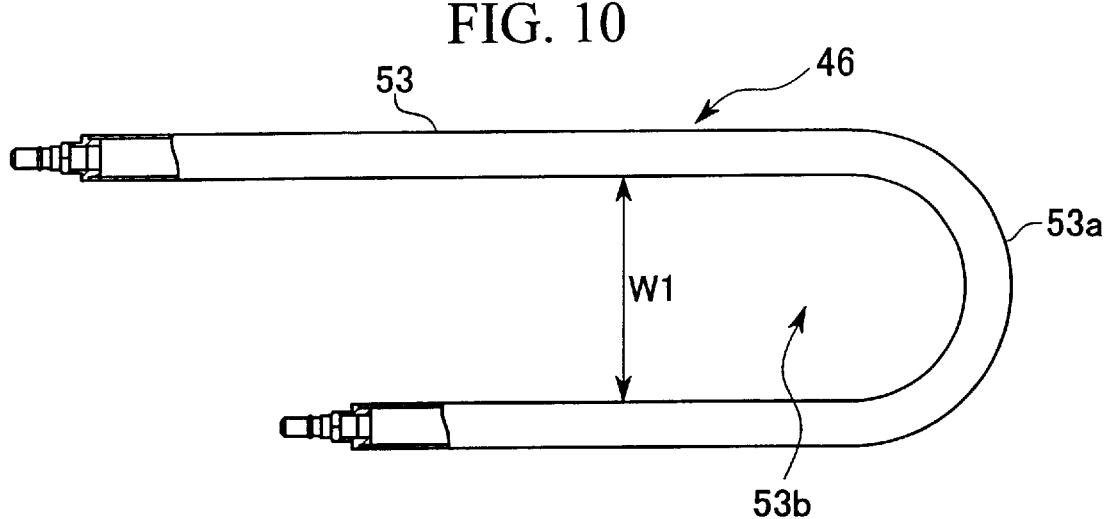
FIG. 10 is a plan view showing a U-shaped pipe which constitutes a cooling pipe in FIG. 7.
Figure 11:
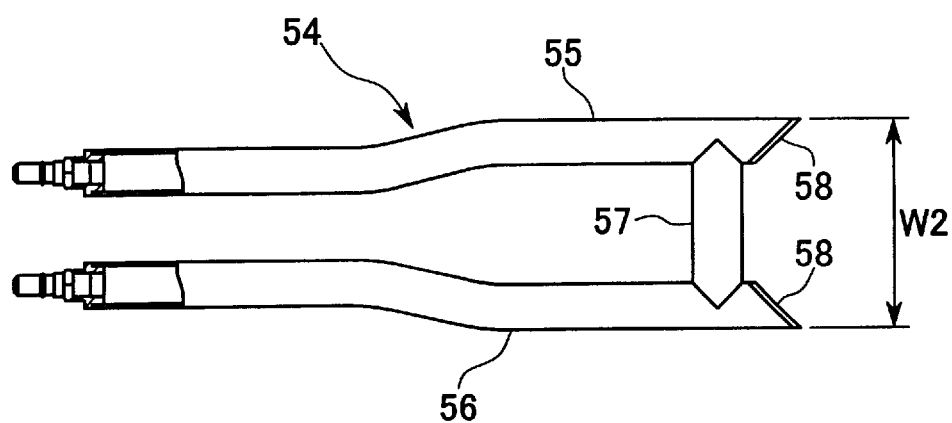
FIG. 11 is a plan view showing a bracket-shaped pipe which constitutes the cooling pipe in FIG. 7.

Each cooling pipe 46 comprises a U-shaped pipe 53 (see FIG. 10) and a bracket-shaped pipe 54 (see FIG. 11). The U-shaped pipe 53 has a curved portion 53a which is curved within one plane in such a way as to have an inside diameter slightly larger than the outside diameter of the steel pipe 1 and have an opening 53b larger than that outside diameter.

The bracket-shaped pipe 54 comprises a first pipe 55 and a second pipe 56, which extend in the horizontal direction in FIG. 11, and a joint pipe 57 which connects the first and second pipes 55 and 56 and extends in the vertical direction in FIG. 11. Plate members 58 and 58 are obliquely attached to the right-hand ends of the first and second pipes 55 and 56, to prevent the coolant that flows inside the pipes from flowing out. The obliquely attached plate members 58 and the joint pipe 57 form an outline which matches the outer surface of the of the steel pipe 1 (see FIG. 13 to be discussed later).

Figure 13:
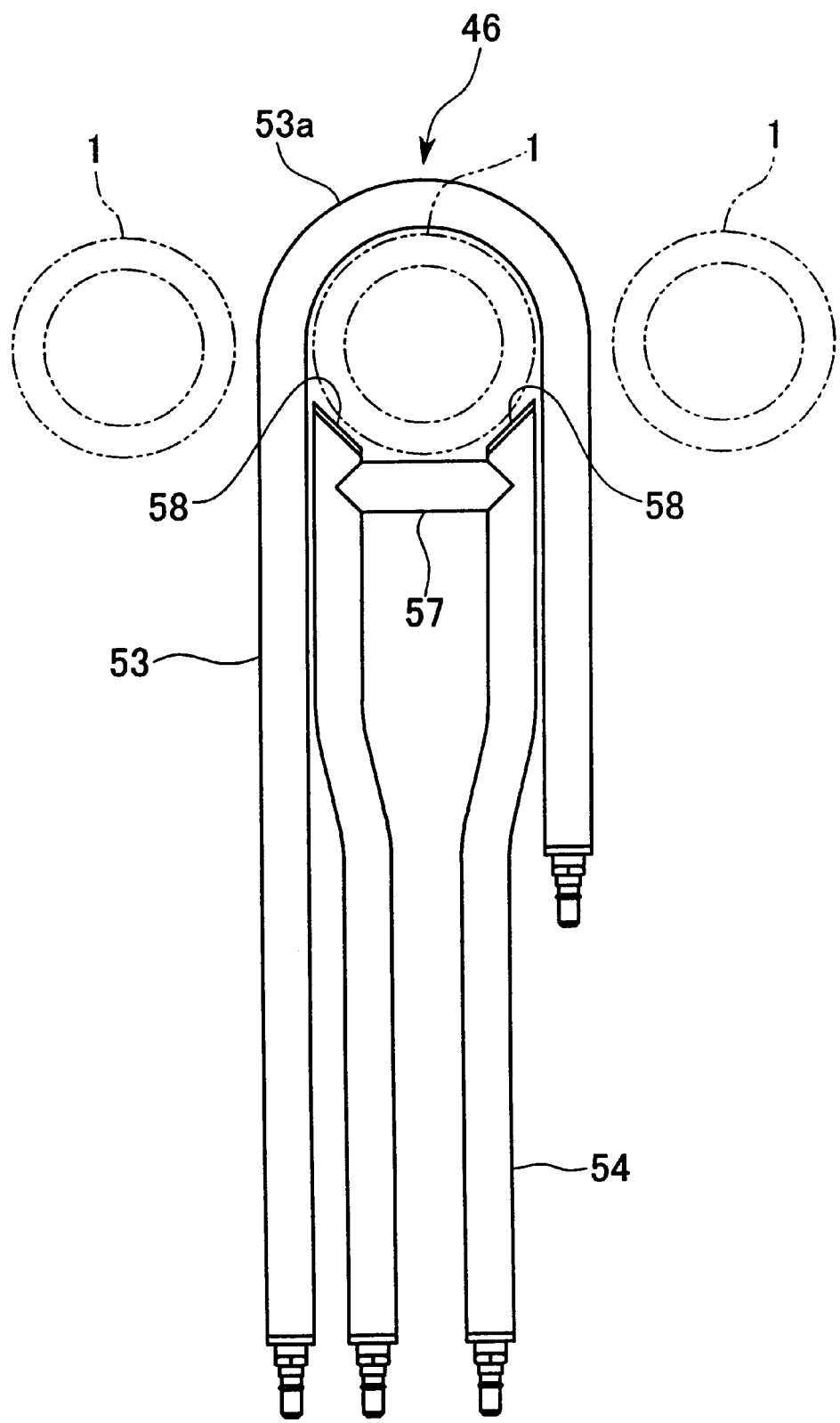
FIG. 13 is a plan view showing the pipes in FIGS. 10 and 11 combined.

The width, W2, between the outer side of the first pipe 55 of the bracket-shaped pipe 54 and the outer side of the second pipe 56 is smaller than the width, W1, of the opening 53b of the U-shaped pipe 53. As shown in FIG. 13, therefore, the U-shaped pipe 53 and the bracket-shaped pipe 54 can be combined in such a manner that the bracket-shaped pipe 54 is put inside the U-shaped pipe 53. With the pipes 53 and 54 combined this way, the curved portion 53a of the U-shaped pipe 53 and the plate members 58 and the joint pipe 57 of the bracket-shaped pipe 54 entirely surround the steel pipe 1.

Figure 12:
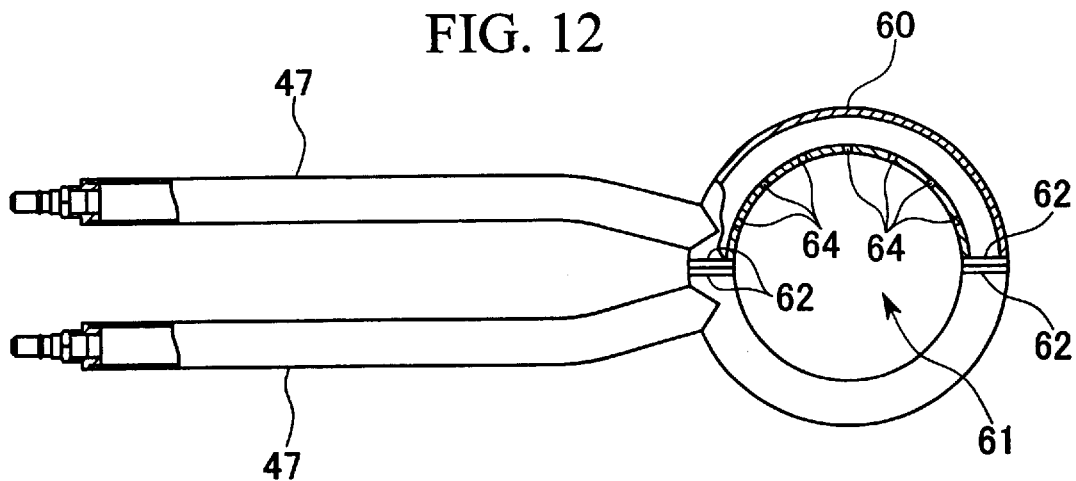
FIG. 12 is a partly cross-sectional, plan view depicting showing a shield-gas feeding pipe in FIG. 7.

Each shield-gas feeding pipe 47 comprises two pipes of the same shape combined symmetrically, as shown in FIG. 12. Each of the two pipes has a curved portion 60 which is curved within one plane in such a way as to have an inside diameter slightly larger than the outside diameter of the steel pipe 1 and have an opening 61 larger than that outside diameter. Plate members 62 are respectively attached to both ends of each curved portion 60 to prevent the shield gas that flows inside each pipe from flowing out. The shield gas is blown out through a plurality of holes 64 formed in the inner wall of the curved portion 60.

Figure 14A:
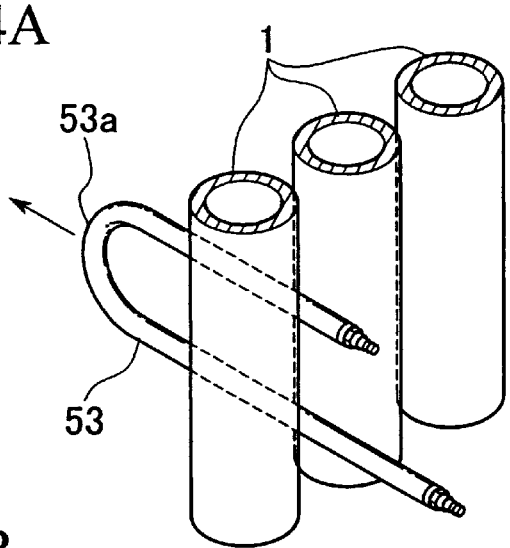
FIG. 14A is a plan view illustrating how to attach the U-shaped pipe in FIG. 10 to a steel pipe with its curved portion inserted between steel pipes.
Figure 14B:
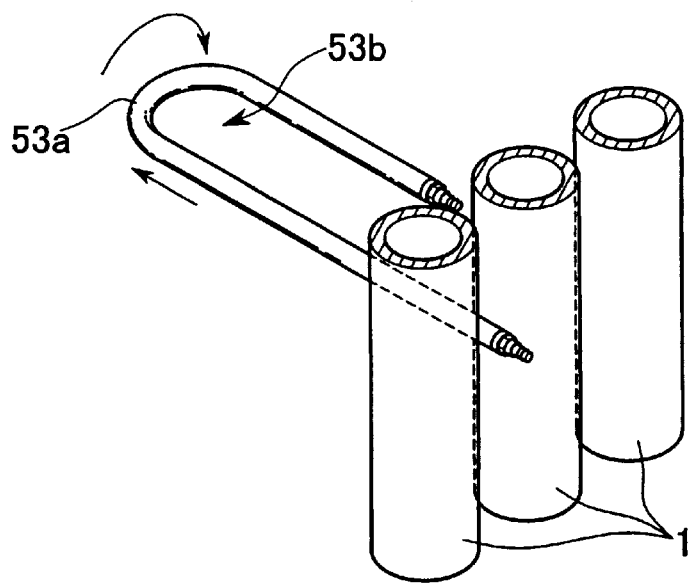
FIG. 14B is a plan view illustrating how to attach the U-shaped pipe in FIG. 10 to a steel pipe with its curved portion turned.
Figure 14C:
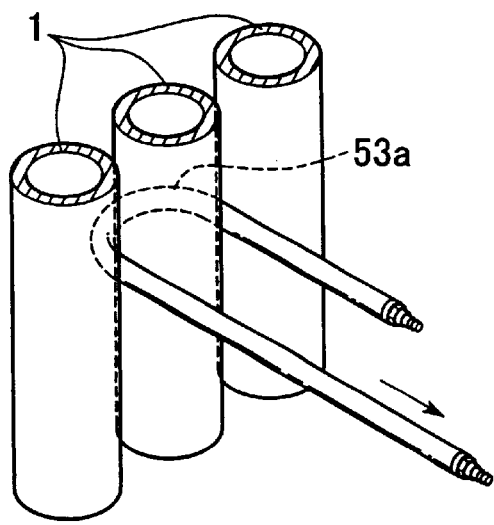
FIG. 14C is a plan view illustrating how to attach the U-shaped pipe in FIG. 10 to a steel pipe with its curved portion pulled back.

Referring now to FIGS. 14A to 14C, a description will be given of how to arrange the U-shaped pipe 53, which constitutes the cooling pipe 46 shown in FIG. 10, around the steel pipe 1.

First, the plane of the curved portion 53a of the U-shaped pipe 53 is set approximately parallel to the upright-standing direction of the steel pipe 1, and the U-shaped pipe 53 is moved forward (see FIG. 14A). This allows the curved portion 53a to be put through between the steel pipes 1 and guided toward the back of the steel pipe 1 from the front side thereof.

Next, the plane is rotated approximately 90° so as to intersect the upright-standing direction of the steel pipe 1 (see FIG. 14B).

Then, the U-shaped pipe 53 is pulled back towards the operator so that the curved portion 53a surrounds the steel pipe 1 (see FIG. 14C).

Repeating the above steps allows a plurality of U-shaped pipes to be positioned one on another around the steel pipe 1.

As the curved portion 53a of the U-shaped pipe 53 is formed in one plane, the curved portion 53a can be put through the space between the adjoining steel pipes 1, even if there is limited space around the target steel pipe 1, by letting this plane pass by the steel pipe 1 in parallel to the upright-standing direction of the steel pipe 1. That is, the curved portion 53a can be put through the space if the space is even only slightly larger than the diameter of the U-shaped pipe 53.

Further, because the curved portion 53a has an opening 53b larger than the outside diameter of the steel pipe 1, the inner surface of the curved portion 53a can be set close to the steel pipe 1 via the opening 53b so that the curved portion 53a surrounds the steel pipe 1.

Although the U-shaped pipe 53 which constitutes the cooling pipe 46 has been explained above with reference to FIGS. 14A to 14C, each heating coil 45 likewise comprises a U-shaped pipe so that, like the U-shaped pipes 53, the U-shaped pipes of the heating coils 45 can be assembled so as to surround the steel pipe 1.

Figure 15A:
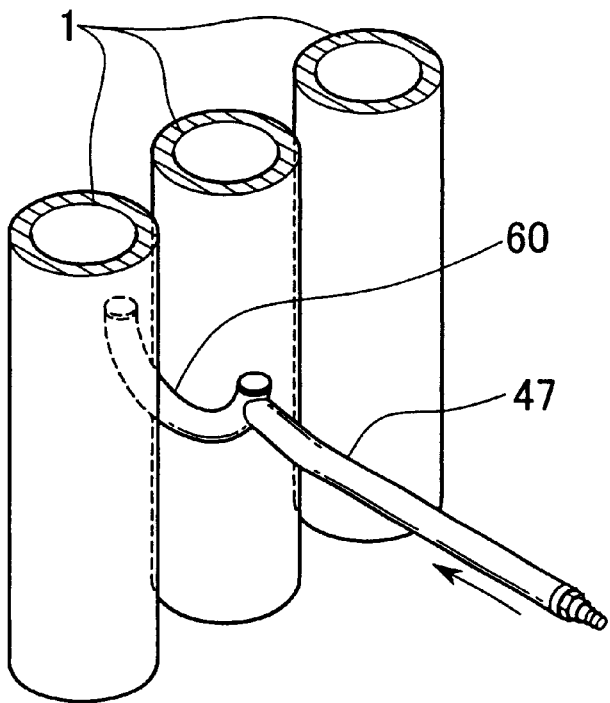
FIG. 15A is a plan view showing how to attach the shield-gas feeding pipe in FIG. 12 to a steel pipe with its curved portion positioned by the steel pipe.
Figure 15B:
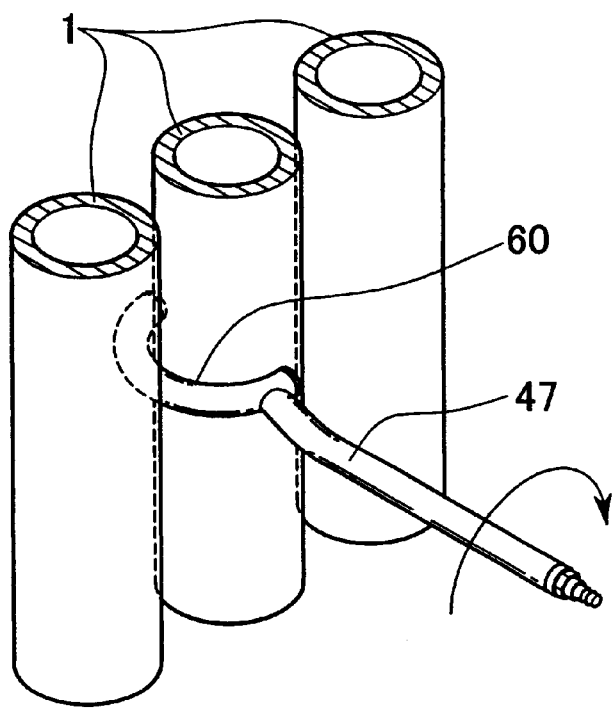
FIG. 15B is a plan view showing how to attach the shield-gas feeding pipe in FIG. 12 to a steel pipe with its curved portion positioned around the steel pipe.

Referring now to FIGS. 15A and 15B, a description will be given of how to arrange the shield-gas feeding pipe 47, shown in FIG. 22, around the steel pipe 1.

First, the plane including the curved portion 60 of one of the two pipes of the shield-gas feeding pipe 47 is set approximately parallel to the upright-standing direction of the steel pipe 1, and one pipe part of the shield-gas feeding pipe 47 is moved forward (see FIG. 15A). As a result, the curved portion 60 is moved forward to the space between the target steel pipe 1 and the adjoining steel pipe 1.

Next, the plane is rotated approximately 90° so as to intersect the upright-standing direction of the steel pipe 1 (see FIG. 15B). This causes the inner surface side of the curved portion 60 to come close to the outer surface of the steel pipe 1.

As the above operations are carried out for both sides of the steel pipe 1, the shield-gas feeding pipe 47 is so positioned as to entirely surround the steel pipe 1. Repeating all the operations can allow the shield-gas feeding pipes 47 to be positioned one on another vertically.

As each curved portion 60 of each shield-gas feeding pipe 47 has the form of one half of a circular pipe which has been segmented into two in the insertion direction (see FIG. 12), positioning the shield-gas feeding pipe 47 around the steel pipe 1 does not require the steps of positioning the curved portion past the space between the adjoining steel pipes 1 and then pulling it back, which are needed for the U-shaped pipe. The shield-gas feeding pipe 47 can be so set that the curved portions 60 surround the steel pipe 1 by simply inserting each pipe of the shield-gas feeding pipe 47 between the steel pipes 1 and turning the pipe by about 90° when the curved portion 60 is positioned by the target steel pipe 1.

Fourth Embodiment

Referring now to FIGS. 16A to 16E, a description will be given of another connecting method which uses the connecting clamp of this invention as the fourth embodiment.

First, a portion around the portion to be mended of the steel pipe 1 is removed and the fins 2 on both sides of the steel pipe 1 are removed so that the connecting clamp 4 can be attached to the steel pipe 1. Next, a new pipe 66 which is slightly shorter than the removed portion of the steel pipe 1 is attached to the steel pipe 1, and then the connecting clamp 4 is attached to an upper portion to be connected 34*a* on which an amorphous sheet (not shown) is provided (see FIG. 16A).

Then, the upper portion to be connected 34*a* is heated by the heating coil while pressure is applied to the upper portion to be connected 34*a* by the upper and lower clamp sections (see FIG. 16B).

In this state, a predetermined gap (distance) G is formed between the ends to be joined of a lower portion to be connected 34*b* (see FIG. 16C).

Further, a heater 68 is attached to the new pipe 66 and the connecting clamp is attached to the lower portion to be connected 34*b* on which an amorphous sheet is provided. Then, the new pipe 66 is heated by the heater 68 so that the new pipe 66 thermally expands, thus reducing the gap G formed the lower portion to be connected 34*b*. Under this situation, amorphous bonding using the connecting clamp 4 is performed (see FIG. 16D).

Next, the heater 68 and the connecting clamp 4 are removed, which completes the mending of the steel pipe 1 (FIG. 16E).

Note that like the heating member 9, the heater 68 may be designed to be separable and provided with a holding lever as shown in FIGS. 6A to 6C showing the second embodiment, so that the heater 68 can be slid around the new pipe 66 at the time of attachment. Alternatively, like the heating coil 45, the heater 68 may be comprised of a U-shaped pipe as shown in FIG. 9, which shows the third embodiment.

Figure 17:
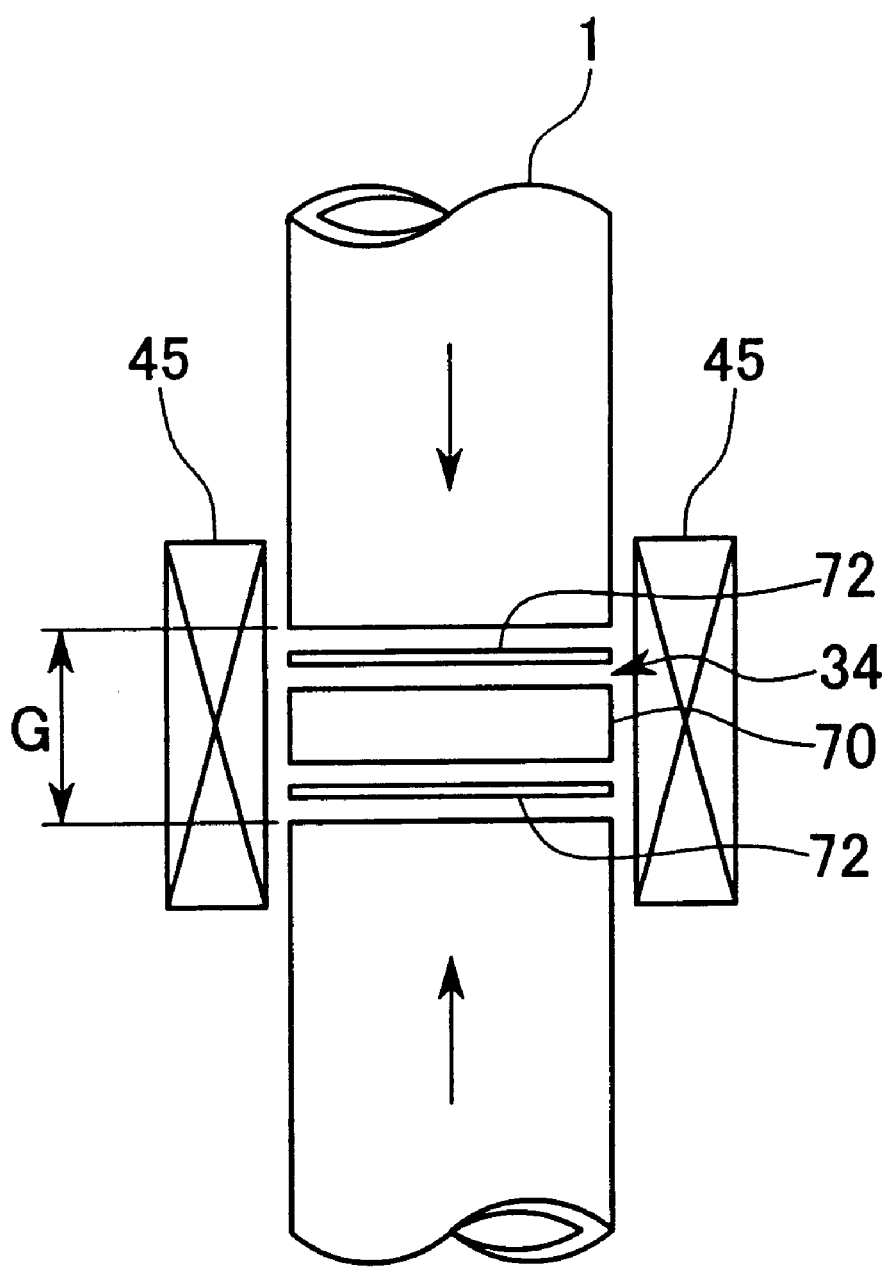
FIG. 17 is a front view showing an insert ring positioned between the ends to be connected.

When the gap G formed the lower portion to be connected 34*b* is large as shown in FIG. 16C, the scheme illustrated in FIG. 17 can be employed.

FIG. 17 is a schematic diagram showing the portion to be connected 34 of the steel pipe 1 surrounded by the heating coil 45. An insert ring (insert member) 70 and amorphous sheets 72 and 72 provided on the opposite sides of the insert ring 70 are positioned between the ends to be joined of the portion to be connected 34. The axial directional length of the insert ring 70 is so set as to cover the gap G and is particularly set shorter than the axial directional length of the heating coil 45. The cross-sectional shape and the material of the insert ring 70 are the same as those of the steel pipe 1.

When an insert ring 70 is sufficiently long to cover the gap G, as shown in FIG. 17, it is unnecessary to cause thermal expansion using the heater 68 as shown in FIG. 16D or it is unnecessary to strongly heat the steel pipe even if the heater 68 is used.

A description will now be given of a method and apparatus for inspecting for defects in a surface bonded by the above-described diffusion bonding method.

Figure 18:
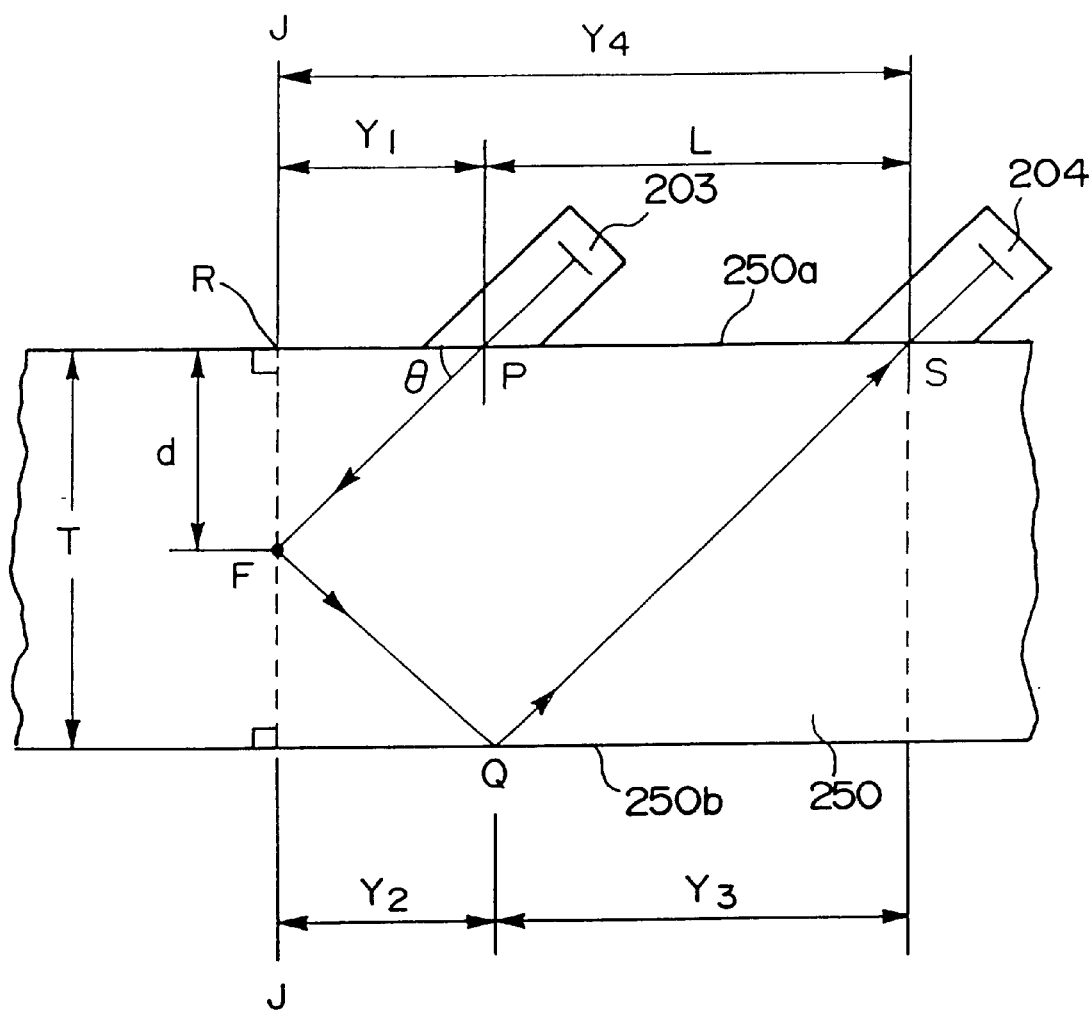
FIG. 18 is a diagram for explaining an inspection method according to this invention.

FIG. 18 is a diagram for explaining the principle of ultrasonic detection using the method of this invention.

In FIG. 18, it is assumed that the material 250 to be inspected has a thickness T and has undergone diffusion bonding so that it has a bonded surface J-J at right angles to the surface, 250*a* of the material 250 to be inspected at a point R and a defect which is produced in the bonded surface J-J from the surface 250*a* is to be inspected.

It is assumed that in the situation shown in FIG. 18, a defect F is detected when the ultrasonic emitting point P of a transmitting probe 203 is separated from the intersection R of the surface 250*a* and the bonded surface J-J by a distance $Y_1$ and the reflected ultrasonic wave is received by receiving probe 204 at point S which is separated from the point P by a distance L. In this case, the emitted ultrasonic wave directly hits the surface to be probed at an angle of θ with respect to the bonded surface J-J, is reflected at a point F, is further reflected once at a point Q on the other surface (bottom surface) 250*b* of the material to be inspected 250, and then reaches the receiving probe 204. According to this invention, it is important that the ultrasonic wave that is transmitted inside the material to be inspected 250 should hit the surface to be probed directly in order to prevent reflection-originated attenuation of the ultrasonic wave to the greatest extent possible.

Given that in FIG. 18, the symbol used are:

T: plate thickness, d: depth to the defect from the surface of the material to be inspected, L: distance between the transmitting probe and the receiving probe, θ: incident angle of the ultrasonic wave, $Y_1$: distance between the bonded surface and the transmitting probe, $Y_2$: distance between the bonded surface and the point of reflection inside the material to be inspected, $Y_3$: distance between the point of reflection inside the to-be-inspected material and the surface of the receiving probe, and $Y_4$: distance between the bonded surface and the surface of the receiving probe, then the following equations apply:

$Y_1 = d \cdot \tan\theta,$ $Y_2 = (T-d) \cdot \tan\theta,$ $Y_3 = T \cdot \tan\theta,$ and $Y_4 = Y_2 + Y_3.$ From the above equations, the distance L between the transmitting probe and the receiving probe and the depth d to the defect from the surface of the material to be inspected satisfy the following relationship.

$$\begin{aligned} L &= Y_4 - Y_1 \\ &= Y_2 + Y_3 - Y_1 \\ &= (T-d) \cdot \tan\theta + T \cdot \tan\theta - d \cdot \tan\theta \\ &= 2 \cdot (T-d) \cdot \tan\theta \end{aligned} \quad (1)$$

Further, the distance L between the transmitting probe and the receiving probe and the distance $Y_1$ between the bonded surface and the transmitting probe satisfy the following relationship.

$$L = 2 \cdot (T \cdot \tan\theta - Y_1) \quad (2)$$

An echo when the transmitting probe 203 is moved from the bonded surface J-J by a distance $Y_1$ can be detected at the position where the distance between the transmitting probe 203 and the receiving probe 204 is L, and the relationship between L and $Y_1$ satisfies the equation 2.

Figure 19:
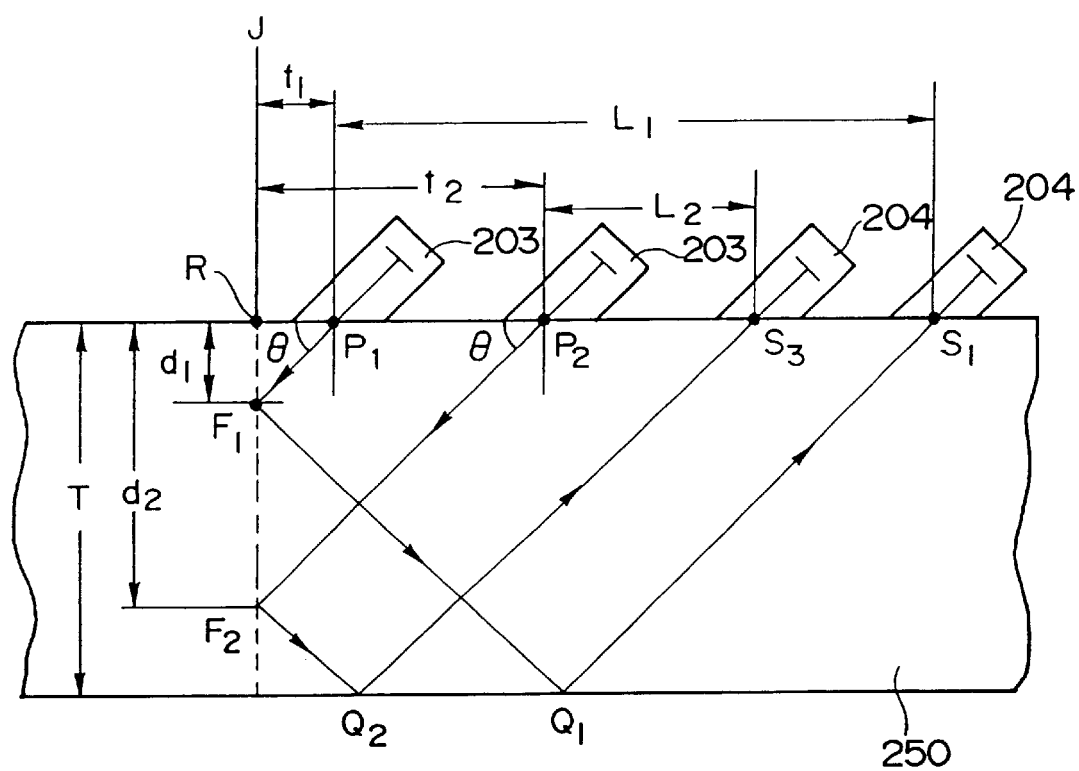
FIG. 19 is a diagram for explaining an example of the inspection method according to this invention.

As the transmitting probe 203 is moved sequentially from the point R on the bonded surface, inner defects present in the thicknesswise direction of the material to be inspected 250 along the bonded surface J-J can be detected sequentially. This is illustrated in FIG. 19, which shows an inner defect $F_1$ at a depth d, and an inner defect $F_2$ at a depth $d_2$. The distance L between the transmitting probe 203 and the receiving probe 204 is $L_1$ in the case of detecting the inner defect $F_1$ and is $L_2$ in the case of detecting the inner defect $F_2$. The distance $Y_1$ (=$t_1$) between the bonded surface and the transmitting probe 203 and the distance L between the transmitting probe 203 and the receiving probe 204 satisfies the relationship given by the equation 2.

As shown in FIG. 19, the distance between the bonded surface J-J and the transmitting probe 203 in the case of detecting the inner defect $F_1$ is $t_1$ and the distance between the bonded surface J-J and the transmitting probe 203 in the case of detecting the inner defect $F_2$ is $t_2$. As the transmitting probe 203 and the receiving probe 204 are moved sequentially, it is possible to detect the depth from the surface of an inner defect. It is understood from FIG. 19 that the deeper an inner defect is from the surface, the shorter the distance L between the transmitting probe 203 and the receiving probe 204. While this method can inspect nearly the entire area of the bonded surface, the minimum value of the distance L between the transmitting probe 203 and the receiving probe 204 is determined by the sizes of the transmitting probe 203 and the receiving probe 204 and cannot be made substantially zero. This limits the depth at which defects can be detected so that there is an undetectable area at the deepest part of the sample.

When there is one reflection of an ultrasonic wave at the surface of the material as shown in FIGS. 18 and 19, an echo appears clearly, thus ensuring excellent detection of minute defects. It is therefore important to receive ultrasonic waves which has been reflected only once. When the position of inspection becomes too deep to secure the distance between the probes, it is inevitable that the ultrasonic wave will be further reflected twice so that the echo which has been reflected three times is to be caught. This is feasible, although the sensitivity is reduced.

Figure 20:
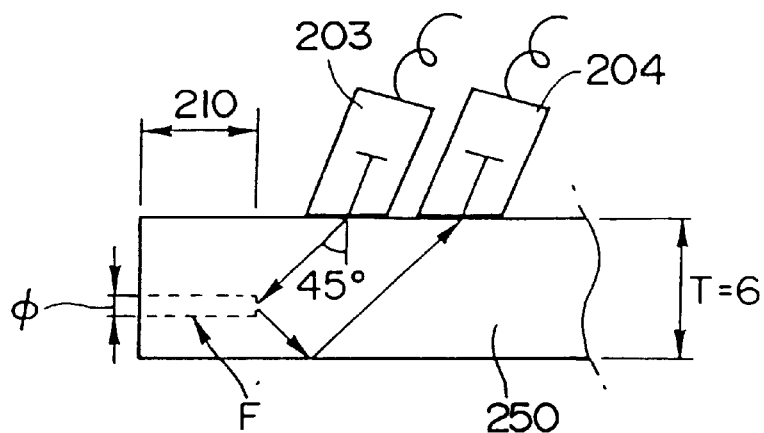
FIG. 20 is a diagram showing the outline of a test for inspecting the measurement precision.
Figure 21:
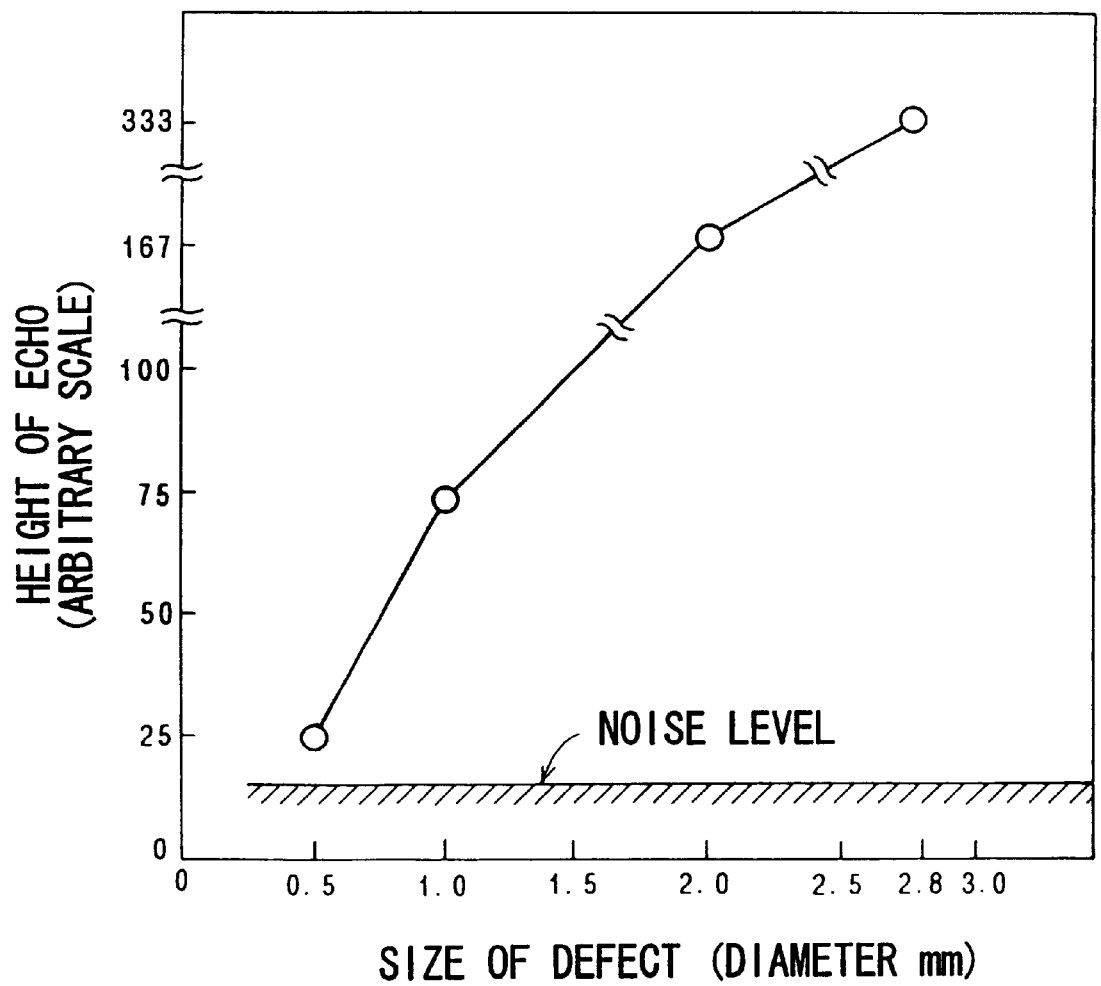
FIG. 21 is a diagram showing the relationship between the size of a defect and the height of an echo.

FIG. 21 shows the results of an experiment for inspecting the detection precision according to the method of this invention. As shown in FIG. 20, a sample can have holes of 0.5 mm to 3.0 mm in diameter, formed horizontally with a length of 10 mm at a depth of 4 mm from the surface of a steel pipe of 6 mm in thickness. An ultrasonic wave is irradiated onto this sample at an angle of 45 degrees, reflected once at the bottom of the steel pipe and the resultant echo is detected. As shown in FIG. 21 which shows the heights of echoes detected this way, it is apparent that this invention can clearly detect even a defect with a diameter of 0.5 mm and is significantly effective in inspecting defects in a diffusion-bonded surface.

Figure 22A:
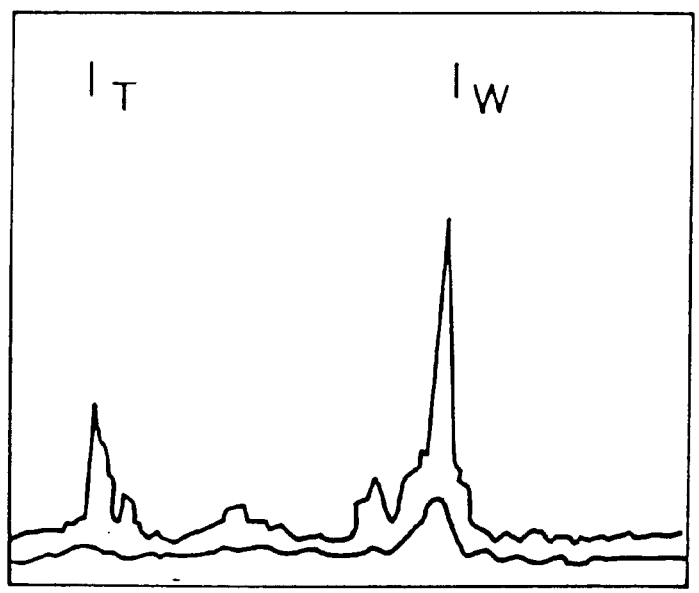
FIG. 22A is a diagram exemplifying an echo according to this invention.
Figure 22B:
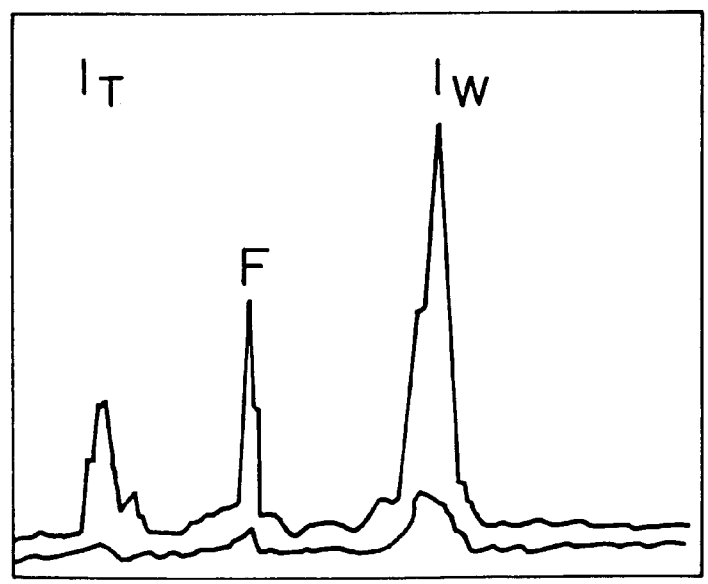
FIG. 22B is a diagram exemplifying an echo according to this invention.

FIGS. 22A and 22B show examples of the behavior of echoes obtained in the aforementioned experiment and shown on a display. In the diagram, It is a pulse echo and Iw is a shape echo from the end face of a to-be-inspected material and neither is relevant to detection of a defect. F is an echo originated from an inner defect. FIG. 22A shows the case where there is no defect and echoes other than the pulse echo and the shape echo show the noise level. FIG. 22b shows the case where there is a defect, and clearly shows a defect echo F. According to the method of this invention, an ultrasonic wave is irradiated directly onto the surface to be probed and the number of reflections at the surfaces of the material to be inspected is suppressed as much as possible, so that the propagation length of the ultrasonic wave is minimized. As a result, the method of this invention reduces the attenuation of the ultrasonic wave and the chances of picking up noise, thus making the echoes clearer and making it possible to detect minute inner defects.

As another embodiment of this invention, a method which reflects an ultrasonic wave incident to a material to be inspected at a predetermined angle once off a surface of the material to be inspected and directly picks up the ultrasonic wave that is reflected at the surface to be probed will be discussed below. In this method, the positions of the transmitting probe 203 and the receiving probe 204 in FIG. 18 are reversed, and the propagation passage of the ultrasonic wave is reversed. While the ultrasonic wave that hits the surface to be probed becomes slightly weaker, the length of the entire propagation passage is the same, and as a result, this method does not raise any practical problems. In this case, the relationship of the equation 2 can be applied as it is except that $Y_1$ should be read as the distance between the bonded surface and the transmitting probe 203.

An apparatus which uses the method of this invention will be discussed below.

Figure 23:
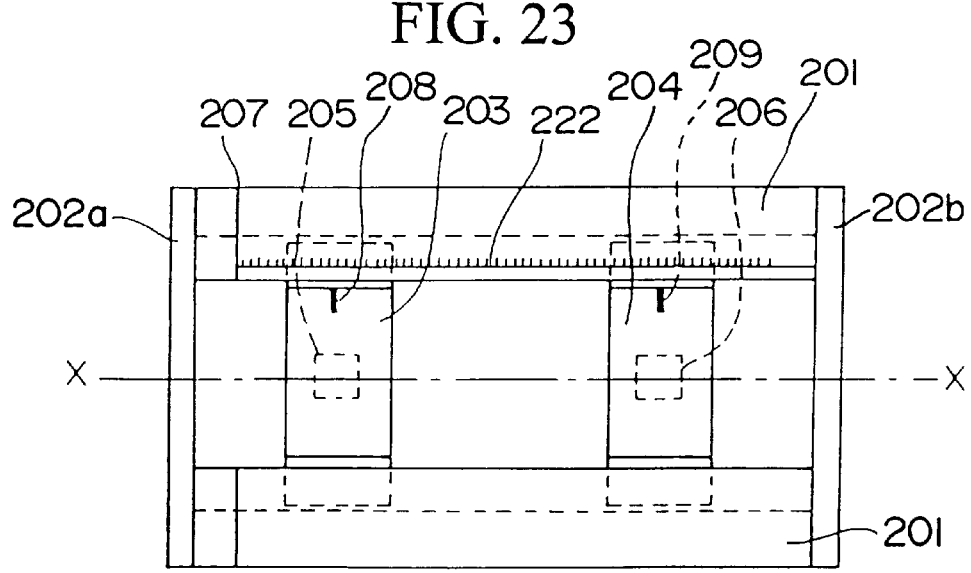
FIG. 23 is a plan view showing one example of an ultrasonic detecting apparatus according to this invention.
Figure 24:
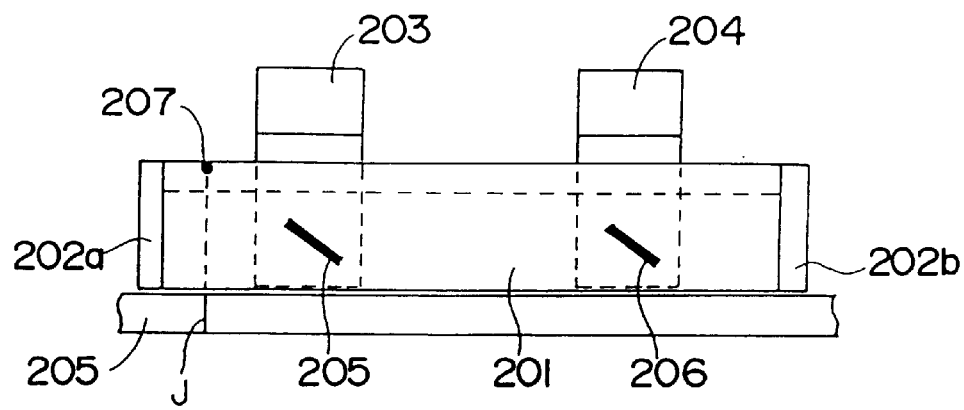
FIG. 24 is a front view of the apparatus shown in FIG. 23.
Figure 25:
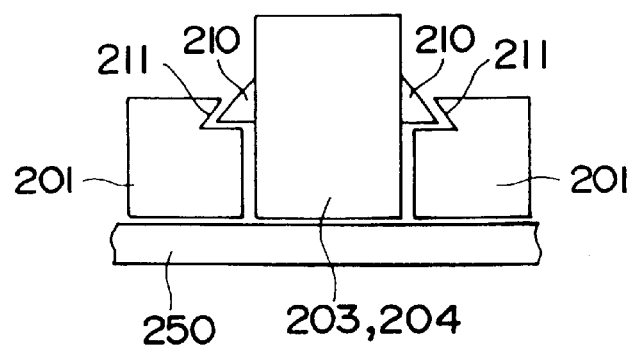
FIG. 25 is a side view of the apparatus shown in FIG. 23.

FIGS. 23 to 25 are diagrams showing one embodiment of an apparatus which uses the method of this invention. FIG. 23 is a plan view, FIG. 24 is a front view, and FIG. 25 is a side view. This embodiment is an example of an apparatus which probes a member acquired by diffusion-bonding a flat plate. The diffusion-bonded surface is formed perpendicular to the surface of the flat plate. In this apparatus, as shown in FIG. 23, both ends of two pedestals 201 are fixed to frames 202a and 202b, thus completing the entire frame. Placed between the opposing two pedestals 201 are the transmitting probe 203 in which a transmitting element 205 is installed and the receiving probe 204 in which a receiving element 206 is installed. Attached to the sides of each of the transmitting probe 203 and the receiving probe 204 are arms 210 which are fitted in grooves 211 formed in the pedestals 201 in such a way as to be slidable in the X-X direction along the pedestals 201. One of the pedestals 201 is provided with a reference line 207 for alignment of the surface to be probed and a scale 222 for computing the distance by which each probe is moved. The distances by which the probes are moved are determined by using markers 208 and 209 which indicate the ultrasonic-wave transmitting and receiving positions of the probes.

The bottom of this apparatus is finished to have a smooth surface so that the bottoms of the pedestals 201 are in the same plane as the bottoms of the transmitting probe 203 and the receiving probe 204 and are closely in contact with the surface of the material to be inspected 250 as shown in FIGS. 24 and 25.

At the time of probing the material to be inspected 250, the reference line 207 of this apparatus is aligned with the surface to be probed J-J so that the center axis X-X of this apparatus is perpendicular to the surface to be probed J-J first. Then, after the marker 208 of the transmitting probe 203 is aligned with the reference line 207, the transmitting probe 203 is moved gradually away from the surface to be probed J-J and the receiving probe 204 is moved in such a way as to maintain the relationship $L=2\times(T \cdot \tan \theta - Y_1)$ according to the equation 2. Probing is carried out this way. At this time, given that the incident angle $\theta$ of the ultrasonic wave is 45 degrees, the equation 2 becomes $L=2\times(T-Y_1)$.

As the apparatus of this invention can be moved freely on a plane, it can detect an inner defect in the diffusion-bonded surface of the plate material with a high precision. For a plate member with a simple surface shape, a single apparatus can be used in various ways.

Next, another example of the apparatus of this invention, which inspects an inner defect in a pipe member, will be discussed below.

The principle of measurement is the same as that of the above-described case of a plate member. It is to be noted, however, that for a pipe member, the bottom of the pedestal and the bottom of the probe should match the curvature of the outside surface of the pipe member and the surface of the pipe member and the bottom of this apparatus should closely contact each other. For pipe members with different outside diameters, an apparatus for detecting inner defects in a pipe member, whose having inter pedestal and probe have bottoms which are changeable according to the outside diameters of pipe members, should be prepared. Such preparation makes it basically possible to detect an inner defect in any pipe member. To facilitate probing of a steel pipe, however, support rollers and a magnet can be further attached to the pedestal according to this invention so that a force of attraction always acts on the steel pipe and the apparatus is movable in the circumferential direction while the apparatus is in close contact with the steel pipe. As another example, an encoder is attached to the pedestal to measure the distance moved in the circumferential direction so that the circumferential position of an inner defect can be known. Further, the signal line of the probe and the signal line of the encoder are made of a shape memory alloy, thus facilitating inspection of the back surface of a pipe member. Examples of the above will be discussed specifically referring to FIGS. 26 and 27.

Figure 26:
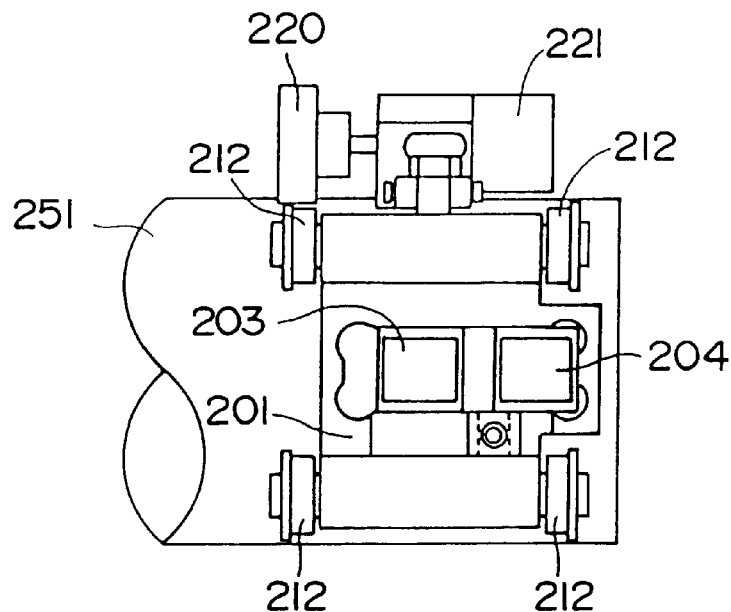
FIG. 26 is a plan view showing another example of the ultrasonic detecting apparatus according to this invention.
Figure 27:
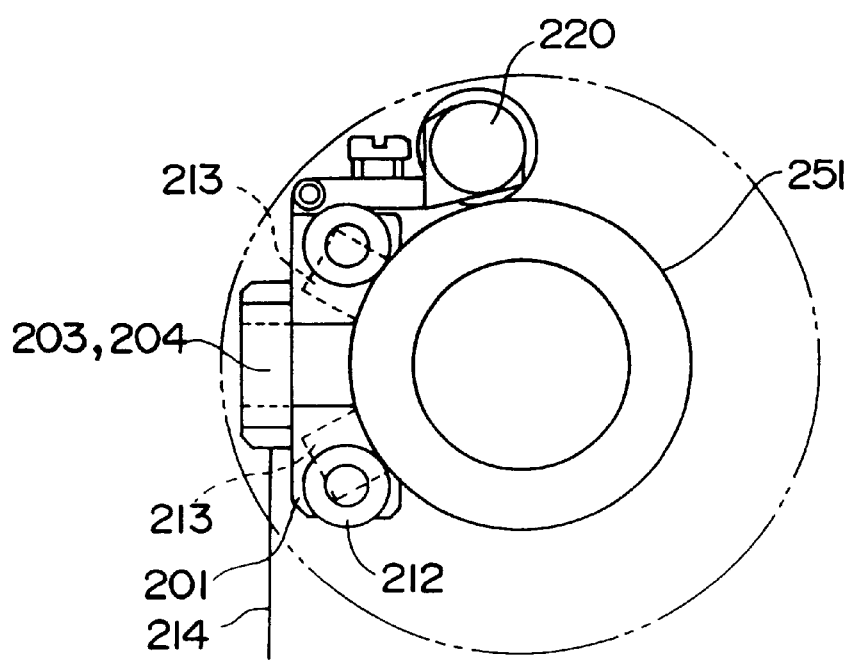
FIG. 27 is a side view of the apparatus shown in FIG. 26.
Figure 28:
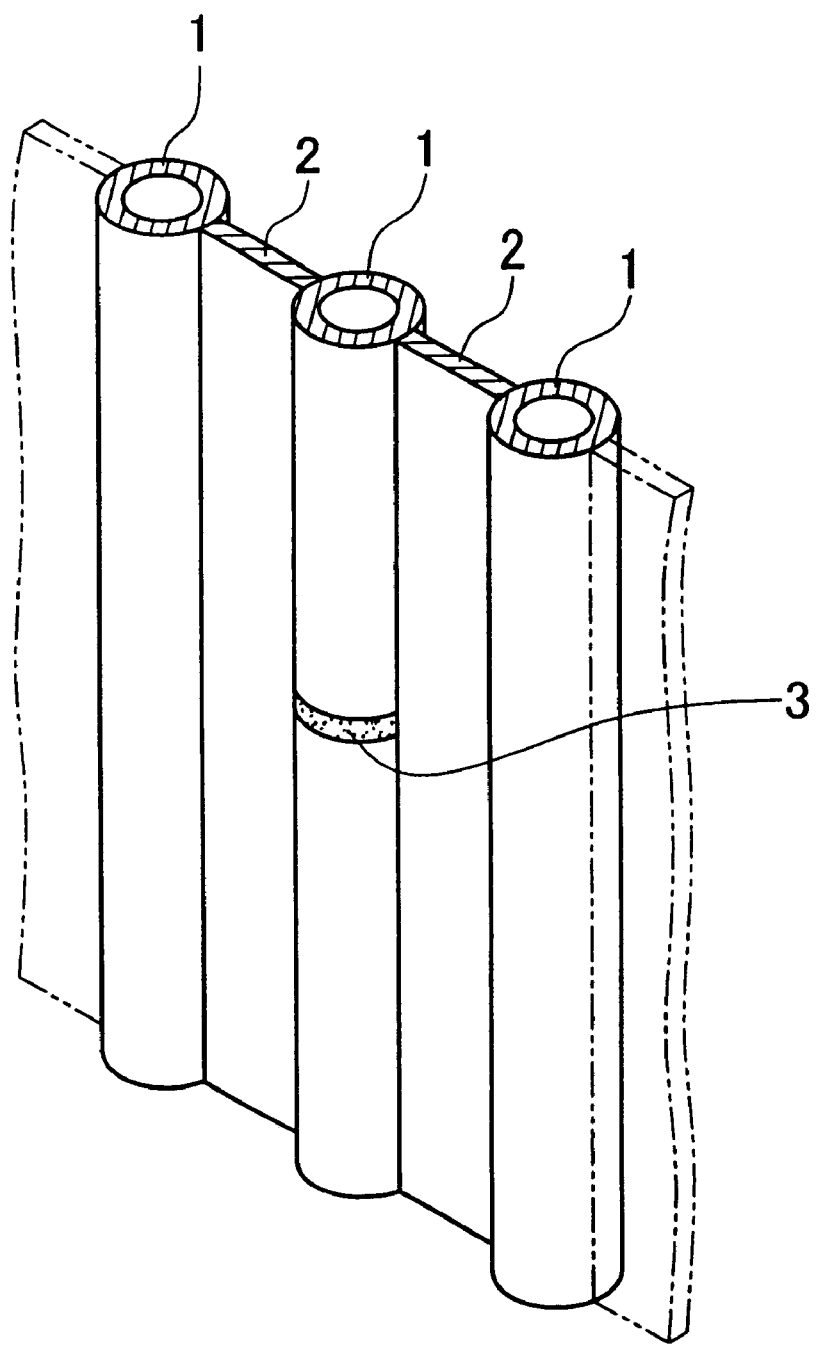
FIG. 28 is a perspective view showing a part of the wall of a furnace.
Figure 29:
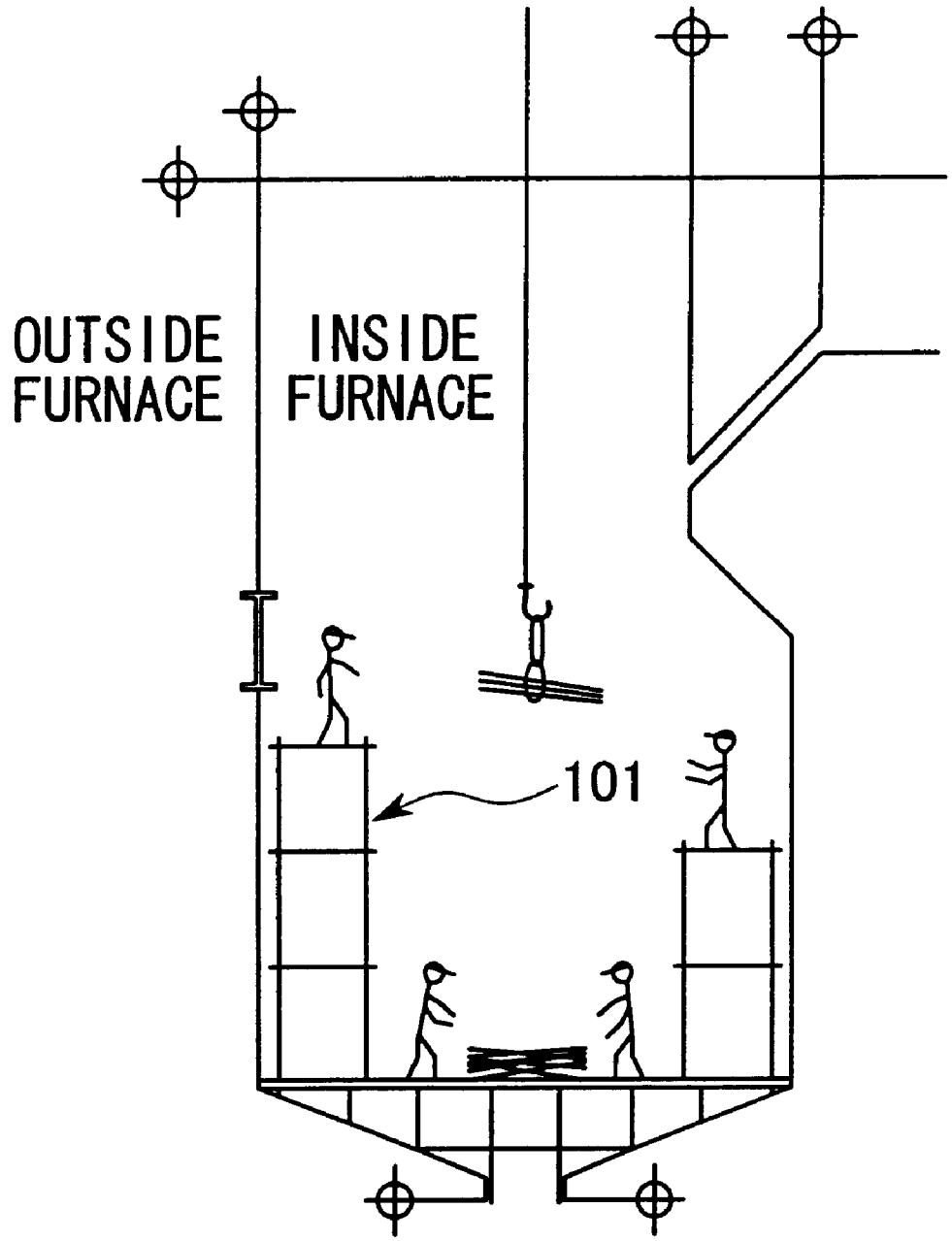
FIG. 29 is a schematic diagram showing a scaffold set up in the furnace.
Figure 30:
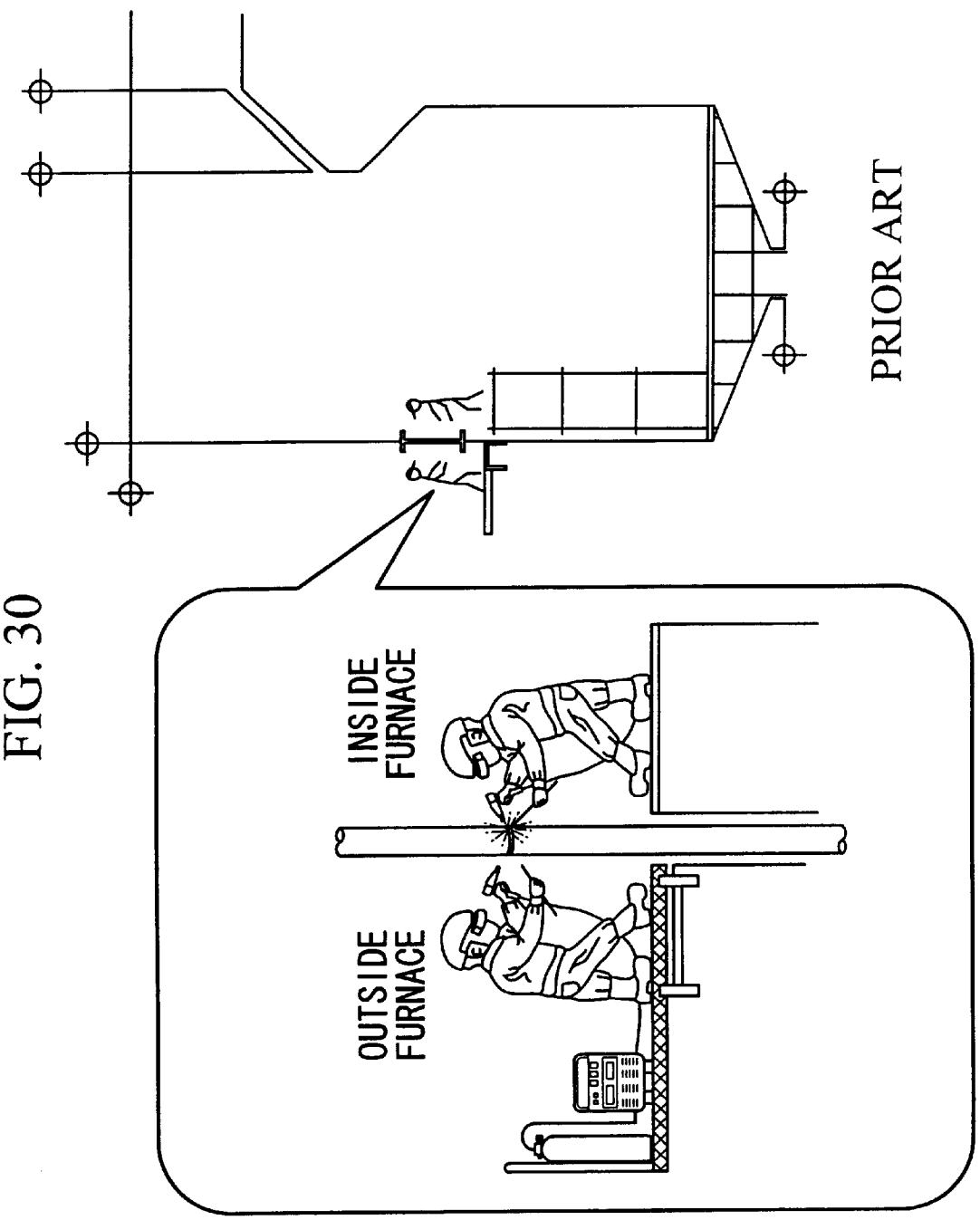
FIG. 30 is a schematic diagram illustrating welding of a steel pipe performed from inside and outside the furnace.
Figure 31:
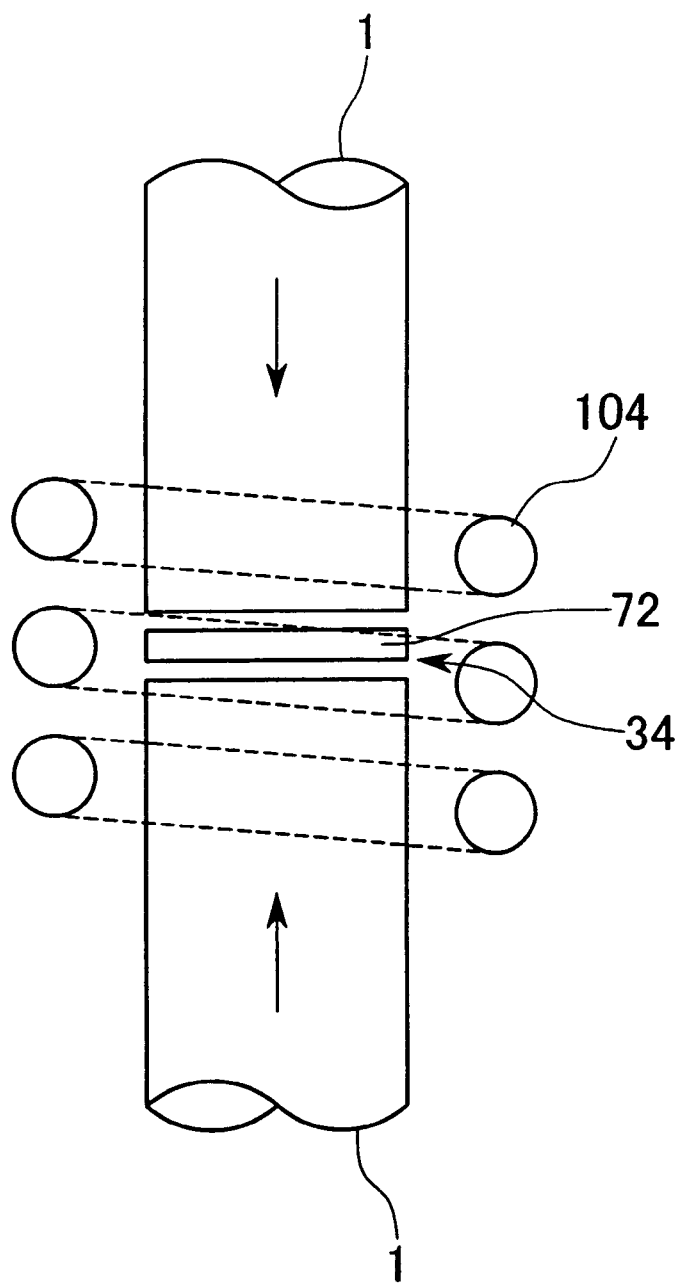
FIG. 31 is a front view schematically showing the conventional amorphous bonding method.
Figure 32:
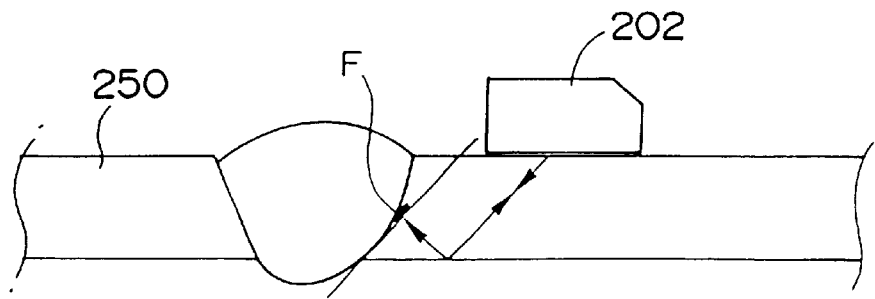
FIG. 32 is a diagram illustrating an inspection method for the conventional fusion bonding.
Figure 33:
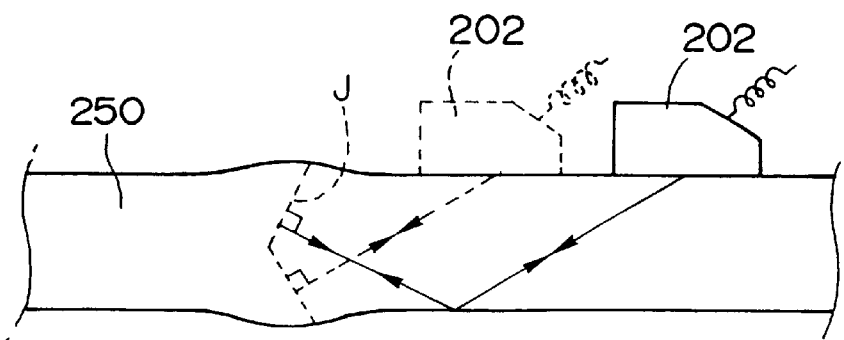
FIG. 33 is a diagram illustrating an inspection method for an improved diffusion-bonded surface.
Figure 34:
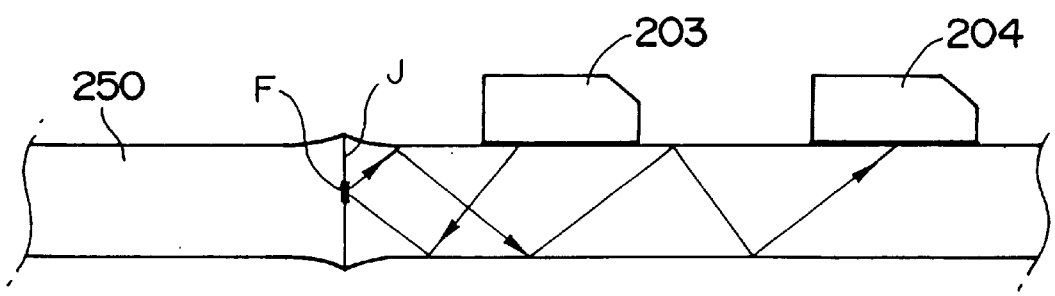
FIG. 34 is a diagram illustrating the conventional inspection method adapted to a diffusion-bonded surface.

FIGS. 26 and 27 show an ultrasonic detecting apparatus for a steel pipe according to this invention. FIG. 26 is a plan view and FIG. 27 is a side view. In FIG. 26, the transmitting probe 203 and the receiving probe 204 are mounted on the center portion of the pedestal 201 on which support rollers 212, an encoder roller 220 and a supplemental unit are further mounted. The probe-sliding mechanism in the vicinity of the transmitting probe 203 and the receiving probe 204 are basically the same as those of a plate member and their detailed descriptions will be omitted.

For the ultrasonic detecting apparatus for a pipe member, the surface of each probe should be matched with the curvature of the outside diameter of a pipe member (steel pipe) 251. In this apparatus, as shown in FIG. 27, the bottoms of the transmitting probe 203 and the receiving probe 204 are integrated with the bottom of the pedestal 201 and are processed to have the same curvature as the outside surface of the pipe member 251. Attached to the pedestal 201 are four support rollers 212 for allowing the entire apparatus to move in the circumferential direction of the pipe member 251. The pedestal 201 may be moved in the circumferential direction of the pipe member 251 manually or by using a drive unit.

Further, a magnet 213 is embedded in the pedestal 201 so as to always pull the apparatus towards the pipe member 251 at the time of inspection. It is therefore possible to easily detect a defect at the back of a pipe member 251 which may be set upright or positioned horizontally. The magnet 213 may be a permanent magnet or an electromagnet. In the case of an electromagnet, the attraction of the magnet 213 can be stopped for separation from the pipe member 251 when the current supply is stopped. As the encoder roller 220 is attached to the pedestal 201, the amount of movement of each probe can be determined when the apparatus is moved in the circumferential direction. Reference numeral "221" denotes an encoder, which permits the position of an inner defect in the circumferential direction of the pipe member 251 to be detected.

A shape memory alloy is used for signal lines 214 of the probe and encoder in the ultrasonic detecting apparatus of this invention. The shape memory alloy used is a Ti—Ni based alloy which contains 49 at % of Ti and 51 a t % of Ni. This shape memory alloy is subjected in advance to a shape-memory heat treatment so as to memorize a curvature greater than the outside diameter of the pipe member 251. The activation temperature of the shape memory alloy is set to 32 to 38° C. to make it adapt the predetermined shape when touched by the hand of an operator. The use of the shape memory alloy for the signal lines 214 allows the signal lines 214, which have arbitrary shapes at the time they are attached to the apparatus, to change their shapes to match the outside diameter of the pipe member 251 when they are touched by an operator's hand when the attachment is completed. This prevents the signal lines 214 from getting entangled at the back of the pipe member 251 and can therefore ensure smooth measurement.

It is possible to supply electric signals, acquired from those signal lines 214, to a micro computer system and display the inspection results as a plan view or a cross-sectional view on a display or print out images. It is also possible to automate detection scanning or attach a plurality of apparatuses to a single long pipe member 251 so that the long pipe member 251 can be probed at plural positions simultaneously.

This apparatus can inspect the entire circumferential direction of a target steel pipe for inner defects, even in the case where, like boiler tubes, thin steel pipes having outside diameters of about 30 mm are positioned at small intervals of about 10 mm and so therebetween.

What is claimed is:

1. A connecting method comprising:
    a wax-material positioning stage of positioning a wax material between connecting ends at a portion to be connected of a rod member,
    a clamp-section attaching stage of positioning a first clamp section and a second clamp section on opposite sides of said portion to be connected and attaching said first and second clamp sections to said rod member; and
    a heating-member attaching stage of attaching a heating member in such a way as to surround said portion to be connected; and
    a connecting stage of connecting said portion to be connected by heating said portion to be connected by said heating member while apply pressure to said portion to be connected by said first and second clamp sections,
    said clamp-section attaching stage including a step of arranging said first and second clamp sections so as to be slid around an outer surface of said rod member from one side of said rod member to the other side thereof,
    said heating-member attaching stage including a step of arranging said heating member so as to be slid around said outer surface of said rod member from said one side of said rod member to said other side thereof.

2. The connecting method according to claim 1, wherein said connecting stage includes a step of heating said rod member so that a distance between said connecting ends of said portion to be connected is decreased by thermal expansion of said rod member.

3. The connecting method according to claim 1, wherein said wax-material positioning stage includes a step of positioning an insert member between said connecting ends and positioning said wax material between said insert member and each of said connecting ends.

4. A connecting method comprising:

a wax-material positioning stage of positioning a wax material between connecting ends at a portion to be connected of a rod member;

a clamp-section attaching stage of positioning a first clamp section and a second clamp section on opposite sides of said portion to be connected and attaching said first and second clamp sections to said rod member; and a heating-member attaching stage of attaching a heating member in such a way as to surround said portion to be connected; and a connecting stage of connecting said portion to be connected by heating said portion to be connected by said heating member while applying pressure to said portion to be connected by said first and second clamp sections, said clamp-section attaching stage including a step of arranging said first and second clamp sections so as to be slid around an outer surface of said rod member from one side of said rod member to the other side thereof, said heating member being provided with a heating coil, a cooling pipe and a shield-gas feeding pipe, each of said heating coil, said cooling pipe and said shield-gas feeding pipe having a curved portion curved in one plane in such a way as to have an inside diameter slightly greater than an outside diameter of said rod member and an opening larger than said outside diameter, said heating-member attaching stage including a step of moving said heating coil, said cooling pipe and said shield-gas feeding pipe forward in such a way that said one plane becomes approximately parallel to an upright-standing direction of said rod member to thereby guide said curved portions from a front side of said rod member toward a rear side thereof, and a stage of rotating said plane in such a way as to become perpendicular to said upright-standing direction, so that said curved portions surround said portion to be connected.

5. The connecting method according to claim 4, wherein said connecting stage includes a step of heating said rod member so that a distance between said connecting ends of said portion to be connected is decreased by thermal expansion of said rod member.

* * * * *